United States Patent
Ressemann et al.

(10) Patent No.: US 10,238,846 B2
(45) Date of Patent: *Mar. 26, 2019

(54) SINUS BALLOON DILATION CATHETERS AND SINUS SURGERY TOOLS

(71) Applicant: ENTELLUS MEDICAL, INC., Plymouth, MN (US)

(72) Inventors: Thomas V. Ressemann, St. Cloud, MN (US); John R. Drontle, Monticello, MN (US); Anthony J. Hanson, Chaska, MN (US); Peter T. Keith, Lanesboro, MN (US)

(73) Assignee: ENTELLUS MEDICAL, INC., Plymouth, MN (US)

( * ) Notice: Subject to any disclaimer, the term of this patent is extended or adjusted under 35 U.S.C. 154(b) by 80 days.

This patent is subject to a terminal disclaimer.

(21) Appl. No.: 14/927,904

(22) Filed: Oct. 30, 2015

(65) Prior Publication Data

US 2016/0151614 A1 Jun. 2, 2016

Related U.S. Application Data

(63) Continuation of application No. 13/671,316, filed on Nov. 7, 2012, now Pat. No. 9,192,748, which is a
(Continued)

(51) Int. Cl.
*A61M 29/00* (2006.01)
*A61M 29/02* (2006.01)
(Continued)

(52) U.S. Cl.
CPC ............ *A61M 29/02* (2013.01); *A61B 1/06* (2013.01); *A61B 17/24* (2013.01); *A61M 29/00* (2013.01);
(Continued)

(58) Field of Classification Search
CPC ............ A61M 29/02; A61M 29/00; A61M 2210/0681; A61M 2210/0618; A61M 25/0662; A61B 1/06; A61B 17/24
See application file for complete search history.

(56) References Cited

U.S. PATENT DOCUMENTS 759,925 A 5/1904 Smith
2,525,183 A 10/1950 Robison
(Continued)

FOREIGN PATENT DOCUMENTS

EP 0129634 1/1985
WO WO 91/17787 11/1991

OTHER PUBLICATIONS

PCT International Preliminary Report on Patentability and the Written Opinion for PCT/US2007/088834, Applicant Entellus Medical, Inc., Forms PCT/IB/326, 373, and PCT/ISA/237 dated Jul. 30, 2009 (9 pages).
(Continued)

*Primary Examiner* — Amy R Weisberg
(74) *Attorney, Agent, or Firm* — Vista IP Law Group LLP

(57) ABSTRACT

Inventive embodiments disclosed herein include a catheter for dilating a sinus cavity lumen. The catheter includes a guide tube, having a proximal end and a distal end, that terminates in a distal tip; a sleeve member annularly positioned over the guide tube, wherein the sleeve member is movable relative to the guide tube and is capable of being advanced over the guide tube; and a balloon coupled to the sleeve member, wherein the balloon can be extendable and inflated at or beyond the end of the guide tube.

7 Claims, 18 Drawing Sheets

Related U.S. Application Data continuation of application No. PCT/US2011/035662, filed on May 7, 2011.

(60) Provisional application No. 61/332,575, filed on May 7, 2010.

(51) Int. Cl.
*A61B 17/24* (2006.01)
*A61B 1/06* (2006.01)
*A61M 25/06* (2006.01)

(52) U.S. Cl.
CPC . *A61M 25/0662* (2013.01); *A61M 2210/0618* (2013.01); *A61M 2210/0681* (2013.01)

(56) References Cited

U.S. PATENT DOCUMENTS

| | | |
|---|---|---|
| 3,312,128 A | 4/1967 | Wasson |
| 3,800,788 A | 4/1974 | White |
| 3,949,750 A | 4/1976 | Freeman |
| 4,417,886 A | 11/1983 | Frankhpuser et al. |
| 4,509,945 A | 4/1985 | Kramann et al. |
| D287,880 S | 1/1987 | Doyle |
| 4,664,113 A | 5/1987 | Frisbie et al. |
| 4,737,141 A | 4/1988 | Spits |
| 4,748,969 A | 6/1988 | Wardle |
| 4,757,827 A | 7/1988 | Buchbinder et al. |
| 4,884,573 A | 12/1989 | Wijay et al. |
| 4,915,684 A | 4/1990 | MacKeen et al. |
| 4,957,117 A | 9/1990 | Wysham |
| 4,988,356 A | 1/1991 | Crittenden et al. |
| 4,994,033 A | 2/1991 | Shockey et al. |
| 5,021,043 A | 6/1991 | Becker et al. |
| 5,024,658 A | 6/1991 | Kozlov et al. |
| 5,084,022 A | 1/1992 | Claude |
| 5,102,390 A | 4/1992 | Crittenden et al. |
| 5,104,376 A | 4/1992 | Crittenden |
| 5,108,414 A | 4/1992 | Enderle et al. |
| 5,117,839 A | 6/1992 | Dance |
| 5,137,517 A | 8/1992 | Loney et al. |
| 5,156,594 A | 10/1992 | Keith |
| 5,163,911 A | 11/1992 | Sirimanne et al. |
| 5,169,386 A | 12/1992 | Becker et al. |
| 5,203,777 A | 4/1993 | Lee |
| 5,253,653 A | 10/1993 | Daigle et al. |
| 5,396,880 A | 3/1995 | Kagan et al. |
| 5,465,528 A | 11/1995 | Schinzel et al. |
| 5,536,248 A | 7/1996 | Weaver et al. |
| 5,545,200 A | 8/1996 | West et al. |
| 5,549,673 A | 8/1996 | Beale |
| 5,555,893 A | 9/1996 | Hackett et al. |
| 5,584,827 A | 12/1996 | Korteweg et al. |
| 5,591,129 A | 1/1997 | Shoup et al. |
| 5,611,775 A | 3/1997 | Machold et al. |
| 5,628,754 A | 5/1997 | Shevlin et al. |
| 5,632,762 A | 5/1997 | Myler |
| 5,645,528 A | 7/1997 | Thome |
| 5,755,695 A | 5/1998 | Erickson et al. |
| 5,755,706 A | 5/1998 | Kronenthal et al. |
| 5,795,325 A * | 8/1998 | Valley ............. A61B 17/12022 604/103.1 |
| 5,827,313 A | 10/1998 | Ream |
| 5,964,767 A | 10/1999 | Tapia et al. |
| 6,013,085 A | 1/2000 | Howard |
| 6,083,188 A | 7/2000 | Becker |
| 6,090,132 A | 7/2000 | Fox |
| 6,113,567 A | 9/2000 | Becker |
| 6,113,587 A | 9/2000 | Negus et al. |
| 6,238,364 B1 | 5/2001 | Becker |
| 6,397,843 B1 | 6/2002 | Tien-Tsai |
| 6,398,743 B1 | 6/2002 | Halseth et al. |
| 6,491,940 B1 | 12/2002 | Levin |
| 6,533,772 B1 | 3/2003 | Sherts et al. |
| 6,543,452 B1 | 4/2003 | Lavigne |
| 6,562,022 B2 | 5/2003 | Hoste et al. |
| 6,743,227 B2 | 6/2004 | Seraj et al. |
| 6,752,800 B1 | 6/2004 | Winston et al. |
| D501,677 S | 2/2005 | Becker |
| 6,851,424 B2 | 2/2005 | Scopton |
| 6,973,352 B1 | 12/2005 | Tsutsui et al. |
| 7,131,969 B1 | 11/2006 | Hovda et al. |
| 7,410,480 B2 | 8/2008 | Muni et al. |
| 7,520,876 B2 | 4/2009 | Ressemann et al. |
| 7,559,925 B2 | 7/2009 | Goldfarb et al. |
| 7,654,997 B2 | 2/2010 | Makower et al. |
| 7,678,099 B2 | 3/2010 | Ressemann et al. |
| 7,717,933 B2 | 5/2010 | Becker |
| 7,842,062 B2 | 11/2010 | Keith et al. |
| 7,879,061 B2 | 2/2011 | Keith et al. |
| 7,918,871 B2 | 4/2011 | Truitt et al. |
| 8,080,000 B2 | 12/2011 | Makower et al. |
| 8,142,422 B2 | 3/2012 | Makower et al. |
| 8,157,766 B2 | 4/2012 | Bonnette et al. |
| 8,241,266 B2 | 8/2012 | Keith et al. |
| 8,277,478 B2 | 10/2012 | Drontle et al. |
| 8,282,667 B2 | 10/2012 | Drontle et al. |
| 8,348,969 B2 | 1/2013 | Keith et al. |
| 8,568,439 B2 | 10/2013 | Keith et al. |
| 8,585,728 B2 | 11/2013 | Keith et al. |
| 8,585,729 B2 | 11/2013 | Keith et al. |
| 8,623,043 B1 | 1/2014 | Keith et al. |
| 8,657,846 B2 | 2/2014 | Keith et al. |
| 8,801,670 B2 | 8/2014 | Drontle et al. |
| 8,834,513 B2 | 9/2014 | Hanson et al. |
| 8,882,795 B2 | 11/2014 | Drontle et al. |
| 8,888,686 B2 | 11/2014 | Drontle et al. |
| 8,915,938 B2 | 12/2014 | Keith et al. |
| 8,986,340 B2 | 3/2015 | Drontle et al. |
| 9,005,284 B2 | 4/2015 | Ressemann |
| 9,011,412 B2 | 4/2015 | Albritton, IV et al. |
| 9,101,739 B2 | 8/2015 | Lesch, Jr. et al. |
| 9,192,748 B2 | 11/2015 | Ressemann et al. |
| 9,278,199 B2 | 3/2016 | Keith et al. |
| 9,282,986 B2 | 3/2016 | Hanson et al. |
| 9,283,360 B2 | 3/2016 | Lesch et al. |
| 9,320,876 B2 | 4/2016 | Ressemann et al. |
| 9,333,327 B2 | 5/2016 | Setliff, III et al. |
| 9,339,637 B2 | 5/2016 | Drontle et al. |
| 9,370,650 B2 | 6/2016 | Hanson et al. |
| 9,433,343 B2 | 9/2016 | Drontle et al. |
| 9,440,049 B2 | 9/2016 | Drontle et al. |
| 9,486,614 B2 | 11/2016 | Drontle et al. |
| 9,550,049 B2 | 1/2017 | Hanson et al. |
| 9,694,167 B2 | 7/2017 | Keith et al. |
| 9,700,705 B2 | 7/2017 | Lesch, Jr. et al. |
| 9,775,975 B2 | 10/2017 | Ressemann et al. |
| 10,022,525 B2 | 7/2018 | Hanson et al. |
| 10,029,069 B2 | 7/2018 | Keith et al. |
| 10,086,181 B2 | 10/2018 | Lesch et al. |
| 2001/0037051 A1 | 11/2001 | Fujii et al. |
| 2002/0010488 A1 | 1/2002 | Crawford et al. |
| 2002/0138121 A1 | 9/2002 | Fox |
| 2003/0032938 A1 | 2/2003 | Altman |
| 2003/0199820 A1 * | 10/2003 | Constantz ......... A61M 25/1011 604/101.04 |
| 2004/0064083 A1 | 4/2004 | Becker |
| 2004/0064150 A1 | 4/2004 | Becker |
| 2004/0133158 A1 | 7/2004 | Keith et al. |
| 2004/0193107 A1 | 9/2004 | Pierpont et al. |
| 2004/0230289 A1 | 11/2004 | DiMatteo et al. |
| 2005/0059931 A1 | 3/2005 | Garrison et al. |
| 2005/0086945 A1 | 4/2005 | Tiemann |
| 2005/0240147 A1 | 10/2005 | Makower et al. |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0063973 A1 | 3/2006 | Makower et al. |
| 2006/0095066 A1 | 5/2006 | Chang et al. |
| 2006/0100687 A1 | 5/2006 | Fahey et al. |
| 2006/0106361 A1 | 5/2006 | Muni et al. |
| 2006/0142704 A1 | 6/2006 | Lentz |
| 2006/0149310 A1 | 7/2006 | Becker |
| 2006/0210605 A1 | 9/2006 | Chang et al. |

(56) References Cited

U.S. PATENT DOCUMENTS

| | | |
|---|---|---|
| 2007/0005094 A1 | 1/2007 | Eaton et al. |
| 2007/0073269 A1 | 3/2007 | Becker |
| 2007/0123926 A1 | 5/2007 | Sater et al. |
| 2007/0129751 A1 | 6/2007 | Muni et al. |
| 2007/0135803 A1 | 6/2007 | Belson |
| 2007/0249896 A1 | 10/2007 | Goldfarb et al. |
| 2007/0250105 A1 | 10/2007 | Ressemann et al. |
| 2008/0015472 A1 | 1/2008 | Ressemann et al. |
| 2008/0015497 A1 | 1/2008 | Keith et al. |
| 2008/0015544 A1 | 1/2008 | Keith et al. |
| 2008/0015626 A1 | 1/2008 | Keith et al. |
| 2008/0033353 A1 | 2/2008 | Truitt et al. |
| 2008/0097295 A1 | 4/2008 | Makower et al. |
| 2008/0125626 A1 | 5/2008 | Chang et al. |
| 2008/0132937 A1 | 6/2008 | Hartley et al. |
| 2008/0172033 A1 | 7/2008 | Keith et al. |
| 2008/0183204 A1 | 7/2008 | Greenhalgh et al. |
| 2008/0249500 A1 | 10/2008 | Keith et al. |
| 2009/0030380 A1* | 1/2009 | Binmoeller ............ A61B 1/018 604/264 |
| 2009/0187098 A1 | 7/2009 | Makower et al. |
| 2009/0216196 A1 | 8/2009 | Drontle et al. |
| 2009/0270835 A1 | 10/2009 | Kushner |
| 2010/0030113 A1 | 2/2010 | Morriss et al. |
| 2010/0076269 A1* | 3/2010 | Makower ............... A61B 1/233 600/178 |
| 2010/0099946 A1 | 4/2010 | Jenkins et al. |
| 2010/0198149 A1 | 8/2010 | Fox |
| 2010/0211007 A1 | 8/2010 | Lesch, Jr. et al. |
| 2010/0274222 A1 | 10/2010 | Setliff et al. |
| 2010/0312101 A1 | 12/2010 | Drontle et al. |
| 2011/0040320 A1 | 2/2011 | Keith et al. |
| 2011/0071349 A1 | 3/2011 | Drontle et al. |
| 2011/0288477 A1 | 11/2011 | Ressemann et al. |
| 2012/0101433 A1 | 4/2012 | Alvarez |
| 2012/0172912 A1 | 7/2012 | Ressemann et al. |
| 2012/0190973 A1 | 7/2012 | Ressemann et al. |
| 2012/0245419 A1 | 9/2012 | Makower et al. |
| 2012/0283625 A1 | 11/2012 | Keith et al. |
| 2013/0030458 A1 | 1/2013 | Drontle et al. |
| 2013/0072958 A1 | 3/2013 | Ressemann et al. |
| 2013/0123833 A1 | 5/2013 | Lesch et al. |
| 2013/0184574 A1 | 7/2013 | Newhauser et al. |
| 2014/0350520 A1 | 11/2014 | Drontle et al. |
| 2014/0357959 A1 | 12/2014 | Hanson et al. |
| 2014/0364700 A1 | 12/2014 | Hanson et al. |
| 2014/0378776 A1 | 12/2014 | Hanson et al. |
| 2015/0031950 A1 | 1/2015 | Drontle et al. |
| 2015/0045827 A1 | 2/2015 | Drontle et al. |
| 2015/0105818 A1 | 4/2015 | Keith et al. |
| 2016/0166814 A1 | 6/2016 | Lesch et al. |
| 2017/0007282 A1 | 1/2017 | Drontle |
| 2017/0028112 A1 | 2/2017 | Drontle et al. |
| 2017/0050001 A1 | 2/2017 | Drontle et al. |
| 2017/0113027 A1 | 4/2017 | Drontle et al. |
| 2017/0368319 A1 | 12/2017 | Lesch et al. |
| 2018/0008806 A1 | 1/2018 | Ressemann et al. |

OTHER PUBLICATIONS

Petersen, Robert J., Canine Fossa Puncture, The Laryngoscope Office, Oct. 5, 1972, pp. 369-371.

Elidan, J., MD., Irrigation of the Maxillary Sinus by Canine Fossa Puncture Experience with 202 Patients, Ann Otol Rhinol Laryngal, 92:1983, pp. 528-529.

Yanagisawa, Eiji, et al., Trans-Canine-Fossa Maxillary Sinoscopy for Biopsy Via the Stammberger Technique, ENT Rhinoscopic Clinic, Aug. 2001 Rhino, pp. 1-3.

Yanagisawa, Eiji, et al., Powered Endoscopic Inferior Meatal Antrostomy Under Canine Fossa Telescopic Guidance, ENT-Ear, Nose & Throat Journal, Sep. 2001, pp. 618-620.

Sathananthar, Shanmugam, et al., Canine Fossa Puncture and Clearance of the Maxillary Sinus for the Severely Diseased Maxillary Sinus, The Laryngoscope 115: Jun. 2005, pp. 1026-1029.

Robinson, Simon, et al., Patterns of Innervation of the Anterior Maxilla: A Cadaver Study with Relevance to Canine Fossa Puncture of the Maxillary Sinus, Laryngoscope 115: Oct. 2005, pp. 1785-1788.

Bolger, William, E., et al., Catheter-Based Dilation of the Sinus Ostia: Initial Safety and Feasibility Analysis in a Cadaver Model, Maryland Sinus Clinic, Bethesda, Maryland, and California Sinus Institute, Palo Alto, California, OceanSide Publications, Inc., May-Jun. 2006, vol. 20, No. 3, pp. 290-294.

Friedman, Michael, M.D. et al., Functional Endoscopic Dilatation of the Sinuses (FEDS): Patient Selection and Surgical Technique, Operative Technologies in Otolaryngology, vol. 17, No. 2, Jun. 2006, pp. 126-134.

Jones, Nick, Commentary on "Safety and Feasibility of Balloon Catheter Dilation of Paranasal Sinus Ostia: A Preliminary Investigation", Annals of Otology, Rhinology & Laryngology 115(4), pp. 300-301 (2006).

Bolger, William E., Commentary Misconceptions Regarding Balloon Catheter Dilation of Paranasal Sinus Ostia, Annals of Otology, Rhinology & Laryngology 115(10): 791-792 (2006).

Lanza, Donald, C., et al., Commentary Balloon Sinuplasty: Not Ready for Prime Time, Annals of Otology, Rhinology & Laryngology 115(10): 789-790 (2006).

Brown, Christopher, L., et al., "Safety and Feasibility of Balloon Catheter Dilation of Paranasal Sinus Ostia: A Preliminary Investigation", Annals of Otology, Rhinology & Laryngology 115(4):293-299 (2006).

Gottman, D., et al., "Balloon Dilatation of Recurrent Ostia Occlusion of the Frontal Sinus", ECR Mar. 3, 2001, 2:-3:30 PM, Vienna Austria (1 page).

Gottman et al., "Balloon Dilation of Recurrent Ostial Occlusion of the Frontal Sinus", Gottmann et al. Abstract (B-0453) Mar. 2001, 22 pages.

PCT International Search Report for PCT/U52007/088834, Applicant: Entellus Medical, Inc., Forms PCT/ISA/220 and PCT/ISA/210, dated May 20, 2008 (4 pages).

PCT Written Opinion for PCT/US2007/088834, Applicant: Entellus Medical, Inc., Form PCT/ISA/237, dated May 20, 2008 (10 pages).

PCT International Preliminary Report for PCT/US2007/088834, Applicant: Entellus Medical, Inc., Form PCT/ISA/237, dated May 20, 2008 (9 pages).

J. M. Robison, Pressure Treatment of Purulent Maxillary Sinusitis, Texas State Journal of Medicine, May 1952, pp. 281-288.

Entellus Medical, 510(k) Letter (Amendment 1) and Attachments D & E, dated Mar. 13, 2008.

Iro, H., J. Zenk. "A new device for frontal sinus endoscopy: First Clinical Report", Department of Otorhinolaryngology, University of Eralngen-Nuremberg, Germany. Otorhinolaryngology, Head and Neck Surgery vol. 125 No. 6, Dec. 2001, pp. 613-616 (4 pages).

PCT International Search Report for PCT/US2011/035662, Applicant: Entellus Medical Inc., Form PCT/ISA/210 and 220, dated Oct. 3, 2011 (4pages).

PCT Written Opinion of the International Search Authority for PCT/US2011/035662, Applicant: Entellus Medical Inc. Form PCT/ISA/237, dated Oct. 3, 2011 (4pages).

PCT International Preliminary Report on Patentability (Chapter I of the Patent Cooperation Treaty) for PCT/US2011/035662, Applicant: Entellus Medical, Inc., Form PCT/IB/326 and 373, dated Nov. 22, 2012 (6pages).

File History of U.S. Appl. No. 13/197,639, Guide Catheter and Method of Use, Inventor: Thomas V. Ressemann, et al., filed Aug. 3, 2011.

Restriction Requirement dated Jun. 11, 2013 in U.S. Appl. No. 13/197,639, filed Aug. 3, 2011, inventor: Thomas V. Ressemann et al., (8pages).

File History of U.S. Appl. No. 13/419,311, Guide Catheter and Method of Use, Inventor: Thomas V. Ressemann, et al., filed Mar. 13, 2012.

Office Action dated Apr. 25, 2012 in U.S. Appl. No. 13/419,311, filed Mar. 13, 2012, inventor: Thomas V. Ressemann, et al., (29pages).

Final Office Action dated Sep. 20, 2012 in U.S. Appl. No. 13/419,311, filed Mar. 13, 2012, inventor: Thomas V. Ressemann, et al., (32pages).

(56) References Cited

OTHER PUBLICATIONS

Mehta, S., Transtracheal Illumination for Optimal Tracheal Tube Placement, Jun. 1989, Anaesthesia, 1989, vol. 44, pp. 970-972.
File History of U.S. Appl. No. 13/419,290, Method of Confirming Location of Guire Wire, Inventor: Thomas V. Ressemann, et al., filed Mar. 13, 2012.
Office Action dated Jul. 12, 2012 in U.S. Appl. No. 13/419,290, filed Mar. 13, 2012, inventor: Thomas V. Ressemann, et al., (9pages).
Office Action dated Dec. 10, 2012 in U.S. Appl. No. 13/419,290, filed Mar. 13, 2012, inventor: Thomas V. Ressemann, et al., (27pages).
Gatot, Albert, et al., "Early treatment of orbital floor fractures with catheter balloon in children", Intl. Journal of Pediatric Otorhinolaryngology, 21 (Apr. 1991) pp. 97-101 (5 pages).
Notice of Allowance dated Sep. 12, 2013 in U.S. Appl. No. 11/782,617, filed Jul. 24, 2007, Inventor: Peter T. Keith et al., (14pages).
Notice of Allowance dated Aug. 12, 2013 in U.S. Appl. No. 13/419,311, filed Mar. 3, 2012, Inventor: Peter T. Keith et al., (17pages).
Notice of Allowance dated Aug. 15, 2013 in U.S. Appl. No. 13/419,290, filed Mar. 13, 2012, Inventor: Peter T. Keith et al., (19pages).
Friedman, Michael, MD., et al., How I do It Rhinology a Targeted Problem and its Solution, Intraoperative and Postoperative Assessment of Frontal Sinus Patency by Transillumination, Laryngoscope 11: Apr. 2000; 663-684.
Office Action dated Jul. 5, 2012 in U.S. Appl. No. 11/782,617, filed Jul. 24, 2007, inventor: Peter T. Keith, (11pages).
Office Action dated Jul. 12, 2012 in U.S. Appl. No. 13/419,290, filed Mar. 13, 2012, inventor: Thomas V. Ressemann, (10pages).
File History of U.S. Appl. No. 11/782,617, Method for Accessing a Sinus Cavity and Related Anatomical Features, Inventor: Peter T. Keith, et al., filed Jul. 24, 2007.
Restriction Requirement dated Oct. 8, 2009 in U.S. Appl. No. 11/782,617, filed Jul. 24, 2007, inventor: Peter T. Keith, (5pages).
Office Action dated Jul. 6, 2010 in U.S. Appl. No. 11/782,617, filed Jul. 24, 2007, inventor: Peter T. Keith, (36pages).
Final Office Action dated Mar. 16, 2011 in U.S. Appl. No. 11/782,617, filed Jul. 24, 2007, inventor: Peter T. Keith, (7pages).
Final Office Action dated Apr. 15, 2013 in U.S. Appl. No. 11/782,617, filed Jul. 24, 2007, inventor: Peter T. Keith, (19pages).
Friedman, Michael, MD., et al., How I do It Rhinology a Targeted Problem and its Solution, Intraoperative and Postoperative Assessment of Frontal Sinus Patency by Transillumination, Laryngoscope, 110, Apr. 2010, pp. 683-684.
Prosecution File History of U.S. Appl. No. 12/355,492, filed Jan. 16, 2009, Inventor: Joshua Makower: Restriction Requirement dated Oct. 9, 2009 (5 pages).
Hoft, J.U.G., et al., Miniature Endoscopes Otorhinolaryngologic Applications, Min Invas Ther & Alied Technol 1998:7/3:209-218.
Prosecution File History of U.S. Appl. No. 11/782,620, filed Jul. 24, 2007, Inventor: Peter Keith, Non-Final Office Action dated Feb. 24, 2010 (33 pages).
Notice of Allowance dated Aug. 3, 2010 in U.S. Appl. No. 11/782,620, filed Jul. 24, 2007, Inventor: Peter Keith.
Prosecution File History of U.S. Appl. No. 12/912,321, filed Oct. 26, 2010, Inventor: Peter Keith, Non-Final Office Action dated May 16, 2012 (19 pages).
Notice of Allowance dated Aug. 3, 2010 in U.S. Appl. No. 12/912,321, filed Oct. 26, 2010, Inventor: Peter Keith; (5 pages).
Prosecution File History of U.S. Appl. No. 11/782,623, filed Jul. 24, 2007, Inventor: Theodore O. Truitt, Non-Final Office Action dated Aug. 18, 2009 (31 pages).
Non-Final Office Action dated Aug. 18, 2009 in U.S. Appl. No. 11/782,623, filed Jul. 24, 2007, Inventor: Theodore O. Truitt, (11 pages).
Final Office Action dated Aug. 30, 2010 in U.S. Appl. No. 11/782,623, filed Jul. 24, 2007, Inventor: Theodore O. Truitt, (8 pages).
Notice of Allowance dated Nov. 22, 2010 in U.S. Appl. No. 11/782,623, filed Jul. 24, 2007, Inventor: Theodore O. Truitt, (6 pages).
Prosecution File History of U.S. Appl. No. 11/782,624, filed Jul. 24, 2007, Inventor: Thomas V. Ressemann, Non-Final Office Action dated Oct. 2, 2009 (33 pages).
Non-Final Office Action dated May 13, 2010 in U.S. Appl. No. 11/782,624, filed Jul. 24, 2007, Inventor: Thomas V. Ressemann, (8 pages).
Non-Final Office Action dated Jun. 3, 2014 in U.S. Appl. No. 11/782,624, filed Jul. 24, 2007, Inventor: Thomas V. Ressemann, (8 pages).
Final Office Action dated Jun. 14, 2015 in U.S. Appl. No. 11/782,624, filed Jul. 24, 2007, Inventor: Thomas V. Ressemann, (9 pages).
Prosecution File History of U.S. Appl. No. 11/782,612, filed Jul. 24, 2007, Inventor: Peter T. Keith, Non-Final Office Action dated Sep. 4, 2009 (35 pages).
Final Office Action dated Mar. 29, 2010 in U.S. Appl. No. 11/782,612, filed Jul. 24, 2007, Inventor: Peter T. Keith, (35 pages).
Notice of Allowance dated Oct. 13, 2010 in U.S. Appl. No. 11/782,612, filed Jul. 24, 2007, Inventor: Peter T. Keith, (6 pages).
Folweiler, David S., Nasal Specific Technique as Part of a Chiropractic Approach to Chronic Sinusitis and Sinus Headaches, Journal of Manipulative and Physiological Therapeutics, vol. 18, No. 1, (Jan. 1995).
International Preliminary Report on Patentability (Chapter I of the Patent Cooperation Treaty) of the International Bureau for PCT/US2007/066187, Applicant: Entellus Medical, Inc., Form PCT/IB/326, dated Oct. 30, 2008 (4 pages).
R. Peterson, Sinus Puncture Therapy; Canine Fossa Puncture Method "How I Do It" Head and Neck, The Laryngoscope 91: Dec. 1981 pp. 2126-2128.
T.G.A. Ijaduola, Use of a Foley Catheter for Short-Tern Drainage of Frontal Sinus Surgery, Journ. of Laryngology and Otology, Apr. 1989, vol. 103, pp. 375-378.
A. Gatot et al., Early Treatment of Oribital Floor Fractures with Catheter Balloon in Children, Inti. J. of Ped. Otorhinolaryngology, 21 (1991) 97-101.
D.I. Tarasov et al., Treatment of Chronic Ethmoiditis by IntraCellular Administration of Medicines to the Ethmoidal Labyrinth, Vestn Otorinolaringol. Nov.-Dec. 1978; (6):45-47 (Abstract in English).
J. M. Robison, Pressure Treatment of Maxillary Sinusitis, J.A.M.A., May 31, 1952, pp. 436-440.

\* cited by examiner

SINUS BALLOON DILATION CATHETERS AND SINUS SURGERY TOOLS

RELATED APPLICATIONS

This Application is a continuation of U.S. application Ser. No. 13/671,316 filed on Nov. 7, 2012, now issued as U.S. Pat. No. 9,192,748, which itself claims priority to PCT Patent Application No. PCT/US2011/035662 filed on May 7, 2011 which itself claims priority to U.S. Provisional Patent Application No. 61/332,575, filed May 7, 2010. The above-noted Applications are incorporated by reference as if set forth fully herein. Priority is claimed pursuant to 35 U.S.C. §§ 119, 120 and any other applicable statute.

FIELD

Inventive subject matter disclosed herein generally relates to balloon inflation devices and methods. More particularly, the field of the invention relates to balloon dilation devices and methods for the treatment of sinusitis.

BACKGROUND

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed, or otherwise has compromised drainage. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has a drainage pathway or outflow tract opening into the nasal passage. This drainage passageway can include an ostium, as well as a "transition space" in the region of the ostia, such as the "frontal recess," in the case of the frontal sinus, or an "ethmoidal infundibulum," in the case of the maxillary sinus. When the mucosa of one or more of the ostia or regions near the ostia become inflamed, the egress of mucous is interrupted, setting the stage for an infection and/or inflammation of the sinus cavity, i.e., sinusitis. Though many instances of sinusitis may be treatable with appropriate medicates, in some cases sinusitis persists for months or more, a condition called chronic sinusitis, and may not respond to medical therapy. Some patients are also prone to multiple episodes of sinusitis in a given period of time, a condition called recurrent sinusitis.

Balloon dilation has been applied to treat constricted sinus passageways for the treatment of sinusitis. These balloon dilation devices typically involve the use of an inflatable balloon located at the distal end of a catheter such as a balloon catheter. Generally, the inflatable balloon is inserted into the constricted sinus passageway in a deflated state. The balloon is then expanded to open or reduce the degree of constriction in the sinus passageway being treated to facilitate better sinus drainage and ventilation. At the same time most, if not all, of the functional mucosal tissue lining of the sinuses and their drainage passageways are preserved.

Exemplary devices and methods particularly suited for the dilation of anatomic structures associated with the maxillary and anterior ethmoid sinuses are disclosed, for example, in U.S. Pat. No. 7,520,876 and U.S. Patent Application Publication No. 2008-0172033. Other systems have been described for the treatment of various other sinuses including the frontal sinus. For example, U.S. Patent Application Publication No. 2008-0097295 discloses a frontal sinus guide catheter (FIG. 6B) and method of treating the frontal sinuses (e.g., FIGS. 8B-8C). U.S. Patent Application Publication No. 2008-0125626 discloses another guide device (e.g., FIGS. 10C and 10C') for transnasal access to the frontal sinuses for treatment.

SUMMARY

Some of the embodiments of the invention disclosed herein include a device for dilating a sinus cavity lumen. The device includes a guide tube, having a proximal end and a distal end that terminates in a malleable distal tip. The device also includes a sleeve member, annularly positioned over the guide tube. The sleeve is movable relative to the guide tube and is capable of being advanced over the guide tube. The device also includes a balloon that is coupled to the sleeve. The balloon is extendable and inflatable at or beyond the end of the guide tube.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Figure 1A:
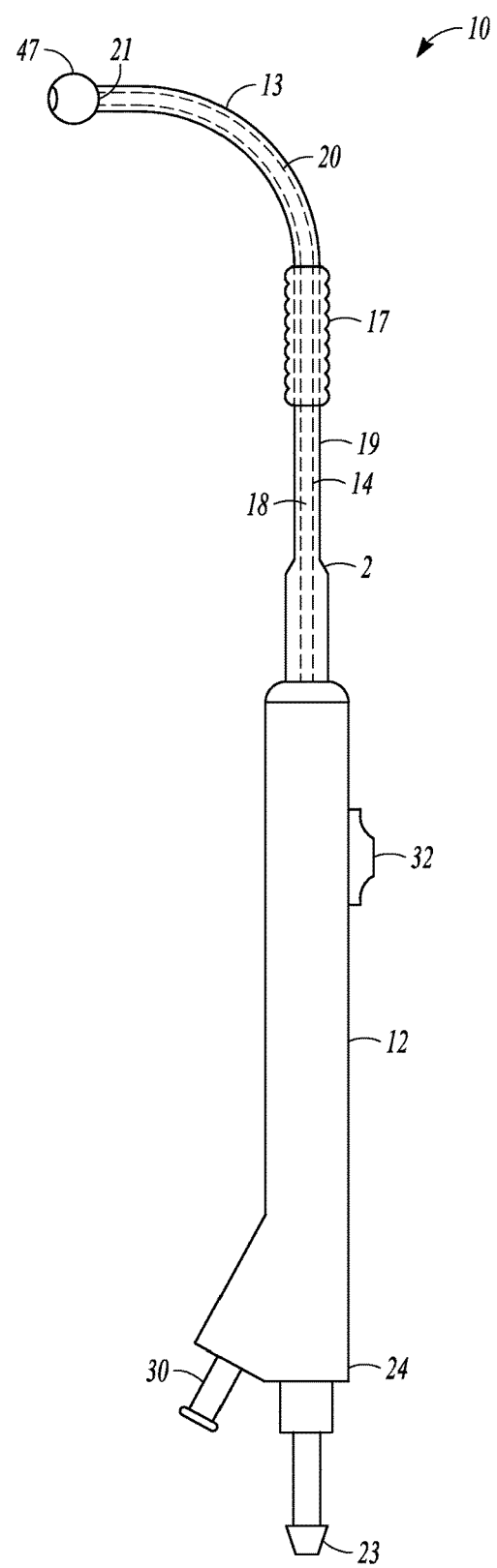
FIGS. 1A and 1B illustrate two views of one embodiment of a balloon dilation catheter of the invention.
Figure 1B:
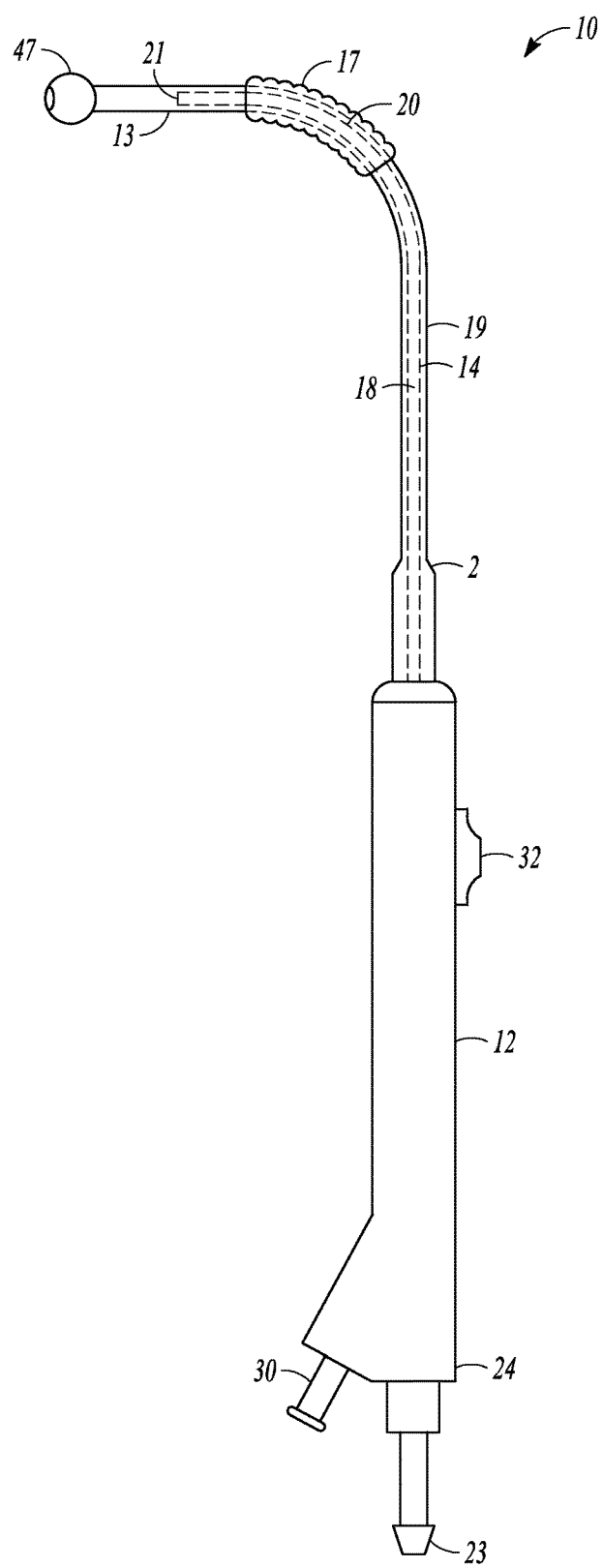

FIGS. 1A and 1B illustrate two views of one embodiment of balloon dilation catheter 10 of the invention. Catheter 10 is useful for treating sinusitis by dilating the sinus ostia or other portions of sinus cavity drainage pathways.

Balloon dilation catheter 10 includes tubular guide 14 having distal end 20 that terminates in malleable distal tip 21. Tubular guide 14 encloses lumen 18 that extends the length of tubular guide 14. Sleeve member 19 also defines a lumen in which is annularly positioned tubular guide 14. Sleeve member 19 is capable of being advanced over tubular guide 14 in a direction parallel with the major axis of tubular guide 14.

Catheter 10 also includes handle 12. Tubular guide 14 is longitudinally static relative to handle 12. Sleeve member 19 is movable longitudinally along tubular guide 14 relative to handle 12. Sleeve member 19 is then not longitudinally static relative to handle 12. Sleeve member 19 includes chamfered distal end 2 which has a enlarged diameter near its proximal end and handle 12 and terminates distally at ball tip 47. Ball tip 47 is positioned at or beyond malleable tip 21 of tubular guide 14. While FIGS. 1A and 1B illustrate an embodiment where sleeve member 19 terminates in ball tip 47 that is positioned at or beyond malleable tip 21 of tubular guide 14, in some embodiments, the sleeve member does not include a ball tip and the sleeve member may terminate at a position that is proximal to the malleable tip of the tubular guide when in a fully retracted state and terminate at a position that is distal to the malleable tip of the tubular guide when in a fully extended state. In further embodiments, the sleeve member does not include a ball tip and the sleeve member terminates at a position that is just distal to, but abuts, the malleable tip of the tubular guide when in a fully retracted state and terminates at a position that is distal to, and does not abut, the malleable tip of the tubular guide when in a fully extended state.

Tubular guide 14 is a malleable stainless steel hypotube and its distal end 20 has a degree of malleability wherein a user may bend or impart a desired shape or configuration to distal end of guide tube 14. As used herein, the term, "malleable" refers to a tip, material, or element of the invention that is capable of being permanently shaped, bent, or otherwise deformed by forces typically produced by manual manipulation of a human user so that the tip, material, or element retains the deformation.

For some embodiments, the proximal end of the tubular guide of any of the catheters described herein is constructed using a material having greater rigidity than the distal end or the malleable tip of the tubular guide. In some embodiments, the tubular guide of any of the catheters described herein is not malleable, but is pre-formed into a particular shape and not intended to be reshaped by the user. In some embodiments, the tubular guide of any of the catheters described herein does not have an internal lumen and is a solid rod.

Tubular guide 14 extends to proximal end 24 of catheter 10 and interfaces in a sealed arrangement with port 23 disposed at proximal end 24. Port 23 provides access to the lumen of tubular guide 14 for the purposes such as irrigation, aspiration, placement of guidewires, illuminated guidewires or devices, or the like.

Distal sleeve portion 13 is constructed from a material that is suitably soft or compliant so it can contact tissue of a sinus ostium or sinus drainage pathway without causing substantial trauma. As used herein, "soft" and "compliant" refers materials or elements of the invention that are capable of being shaped, bent, or otherwise deformed by relatively small forces (e.g., those typically produced by manual manipulation of a human user or from slight pressure by being pressed against tissue) but do not retain the deformation once the force is removed. "Soft" and "complaint" materials are not malleable. Suitable soft or compliant materials can include silicone and thermoplastic materials (e.g., polyethylene or PEBAX). In other embodiments, at least the distal sleeve portion of a sleeve member is formed from a material that is malleable so that the distal sleeve portion can be shaped and the distal sleeve portion can maintain its shape. In some embodiments, the distal sleeve portion of a sleeve member 19 is constructed of a soft and deflectable material while the tubular guide 14 is constructed of a more rigid, though malleable, stainless steel hypotube.

Tubular guide 14 may be pre-shaped to have a bend as is illustrated in distal end 20 in FIGS. 1A and 1B. The nature and degree of the bend may be configured to match with the frontal sinus tract or frontal recess. For other embodiments, the distal end of the tubular guide is malleable and is not pre-shaped in the form of the bend illustrated in FIGS. 1A and 1B.

Balloon 17 is positioned on or incorporated into sleeve member 19 and travels with sleeve member 19 longitudinally over the length of tubular guide 14. Balloon 17 is mounted on sleeve member 19 so as to form a fluidic seal between balloon 17 and inflation lumen 30. Balloon 17 is bonded to sleeve member 19 using a weld, adhesive, or the like. In another embodiment, the balloon is secured to the sleeve member using a mechanical connection. Generally, any technique known to those skilled in the art may be used to secure to the balloon to the sleeve member. Given that balloon 17 is secured directly to sleeve member 19, both structures are slidably mounted over tubular member 14.

Sleeve member 19 is mechanically linked to pushing member 32 and the other components of handle 12 in a manner similar to that illustrated in FIG. 2E and described with reference to balloon dilation catheter 210 (described below). In use, a practitioner of catheter 10 holds handle 12 and, using one of his/her fingers, slides pushing member 32 towards the distal end of handle 12. As pushing member 32 is translated towards distal end of handle 12, sleeve member 19 translates along the length of tubular guide 14. Ball tip 47 and distal sleeve portion 13 move distally along the longitudinal length distal end 20 of tubular guide 14. With increased translation of pushing member 32, an increasing length of distal sleeve portion 13 translates off distal tip 21 of distal sleeve portion 13. With sufficient translation of pushing member 32, all or some portion of the length of distal sleeve portion 13 and all or some portion of balloon 17 can be directed longitudinally off of distal tip 21. In this manner, some or all of distal sleeve portion 13 or balloon 17 can be extended distally off of tubular guide 14 and relative to handle 12.

The interior portion of balloon 17 is in fluid communication with inflation port 30 via an inflation lumen (not illustrated in FIG. 1A or 1B) defined by the distal portion of sleeve member 19. An inflation device (not illustrated) may be connected to inflation port 30 and a fluid (e.g., liquid water). One exemplary inflation device that may be used in connection with balloon dilation catheter 10 is described in U.S. patent application Ser. No. 12/372,691, which was filed on 17 Feb. 2009, published as U.S. Pat. Pub. 2010/0211007 and is incorporated by reference as if set forth fully herein. Other inflation devices may also be used.

Balloon dilation catheter 10 is shown in a retracted position in FIG. 1A and in an extended position in FIG. 1B. In the retracted position, sleeve member 19 and balloon 17 are positioned over tubular guide 14 and ball tip 47 of sleeve member 19 abuts distal end 20 of tubular guide 14. In the extended position illustrated in FIG. 1B, most of distal sleeve portion 13 has translated distally off of distal tip 21 of malleable distal end 20 of tubular guide 18 and balloon 17 is now positioned on distal end 20 and more proximal to distal tip 21. In the retracted position, the entire length of sleeve member 19 is directly supported by the more rigid tubular guide 14 and catheter 10 can be used as a probing instrument that will provide relatively good tactile feedback. In the extended position shown in FIG. 1B, distal sleeve portion 13 is no longer directly supported by the more rigid tubular guide 14 is more deflectable than compared to when it is in the retracted position and catheter 10 can be used as a probing instrument with distal portion that is less likely to traumatize tissue.

In some embodiments (e.g., embodiments where the distal sleeve portion does not include a ball tip), when the balloon dilation catheter is in a fully retracted position, some portion or all of a distal end of a tubular guide extends out from the distal end of sleeve member and is exposed. In such embodiments, when the balloon dilation catheter is placed in an extended position, the distal sleeve portion and possibly some portion or all of the balloon is translated past the malleable distal end of the tubular guide such that the entire length of the tubular guide becomes enveloped by the sleeve member and no portion of the tubular guide is exposed.

In operation, catheter 10 is directed into a patient's nasal cavity and the distal portions of catheter 10 can be used to probe sinus passageways in order to find a desired dilation treatment site. In a fully retracted position, catheter 10 is a tool that provides the user relatively good tactile feedback during his/her probing. If desired, a user may extend distal sleeve portion 13 off of distal end 20, thereby providing catheter 10 a less rigid and more deflectable distal portion, relative to the retracted position, with which he/she can probe the sinus anatomy in a manner that is less likely to cause trauma to contacted tissue. Once the physician identifies the treatment site, the physician positions balloon 17 in the desired location, either by manipulating the entire catheter 10, translating balloon 17 along tubular guide 14, or both. The physician can then inflate balloon 17 using an inflation device that is in fluid communication with inflation lumen 30.

Port 23 may be configured with a conventional interface (e.g., a Luer connector) and may be used as an aspiration port or a port for directing fluids and/or medicaments through lumen 18 and out ball tip 47. Alternatively, or in addition, a guidewire can be directed through port 23 and lumen 18 and out of ball tip 47 in order to assist a user in positioning catheter 10 in a desired portion of a patient's anatomy.

Figure 2A:
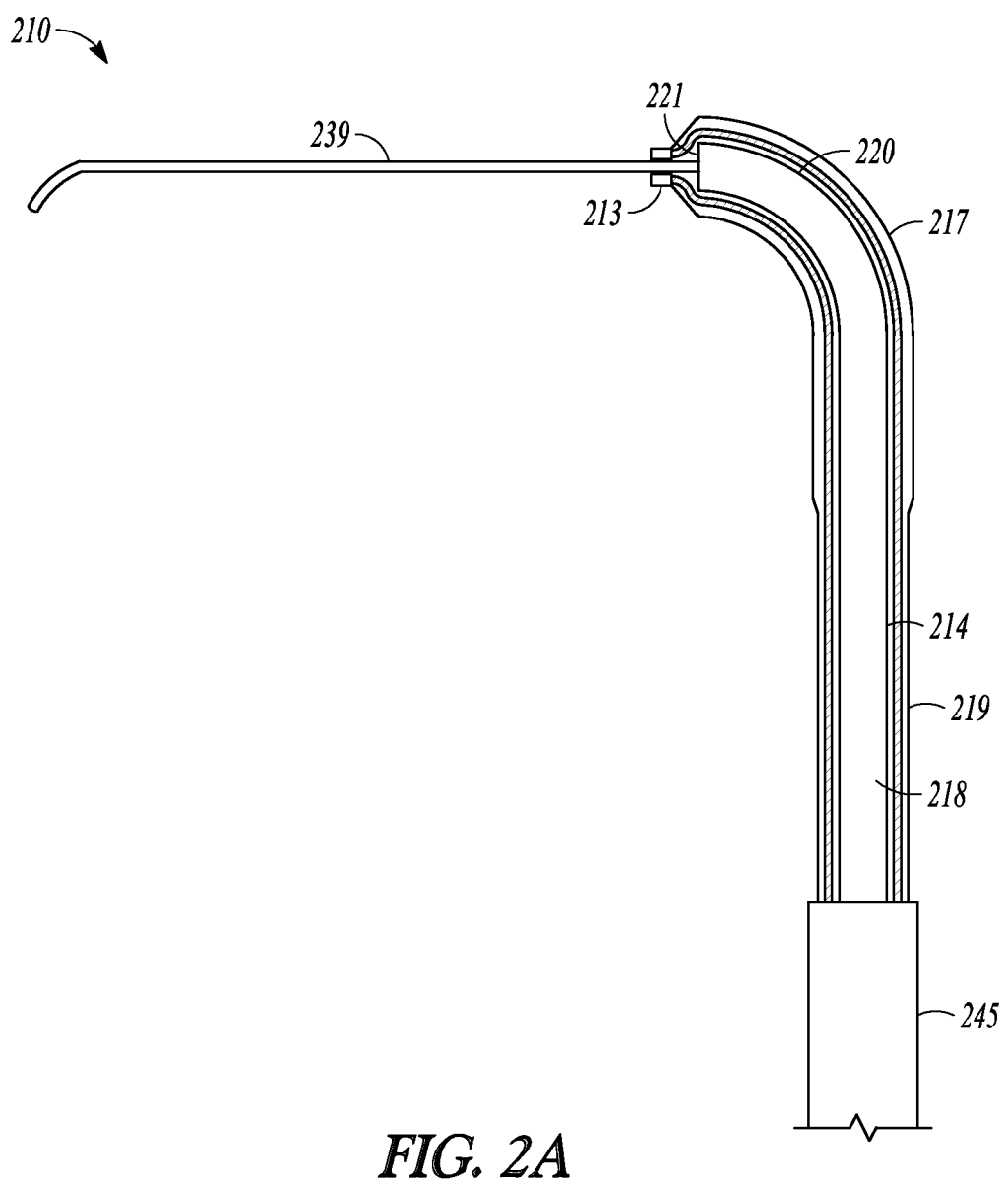
FIGS. 2A-2C illustrate partial cut-away views of a distal end portion of a balloon dilation catheter of the invention showing a sequential extension and dilation of a balloon.
Figure 2B:
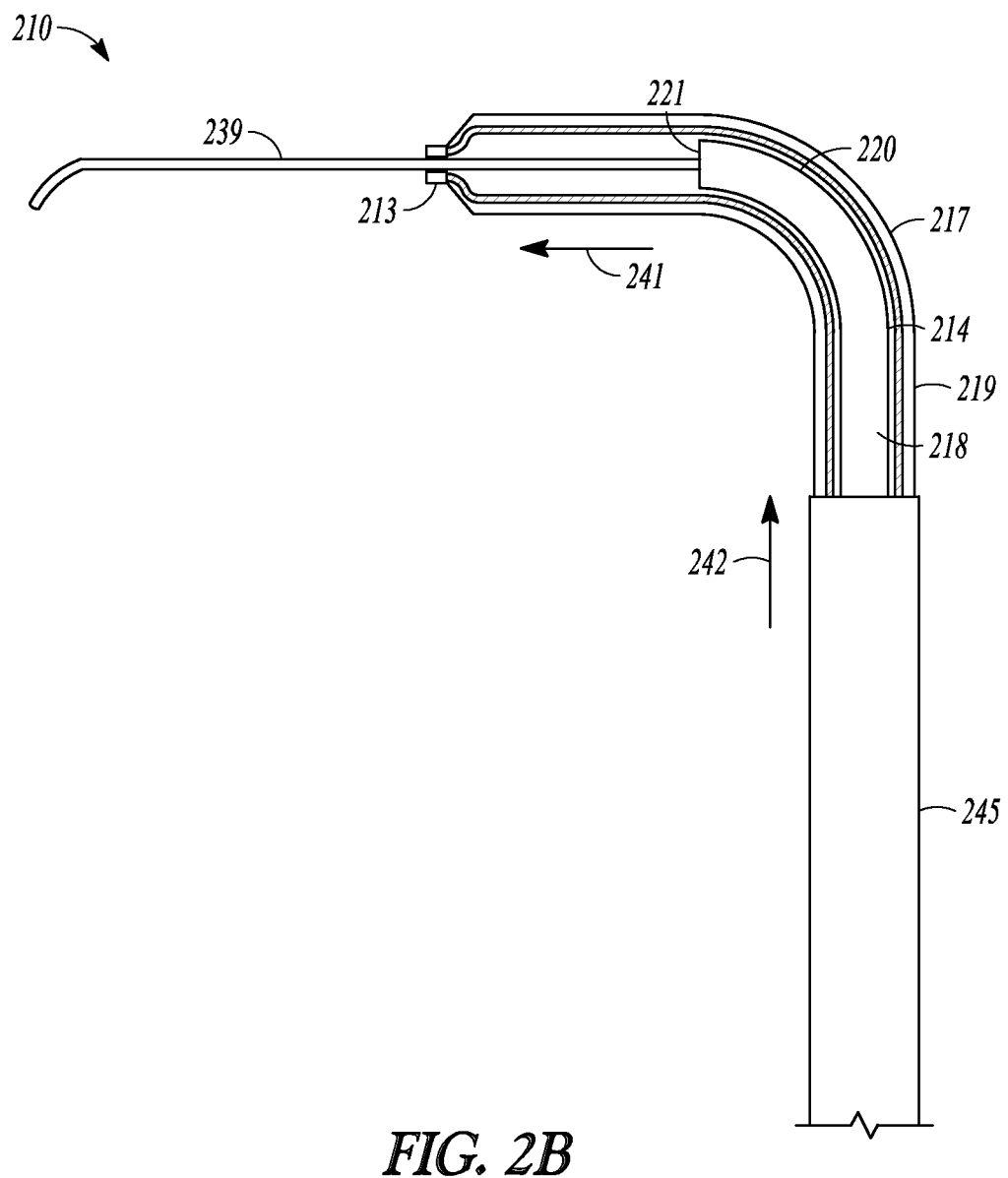
Figure 2C:
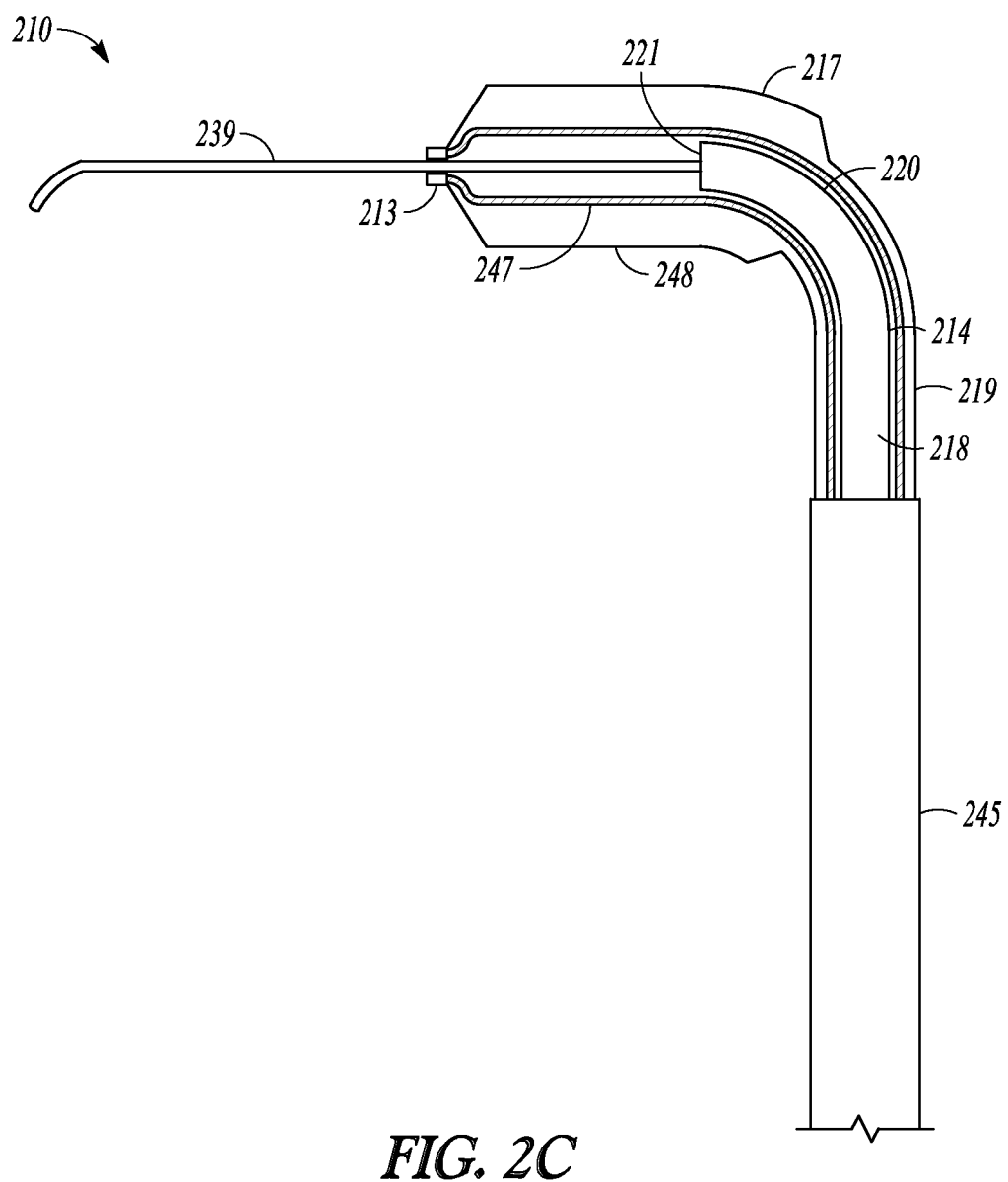
Figure 2D:
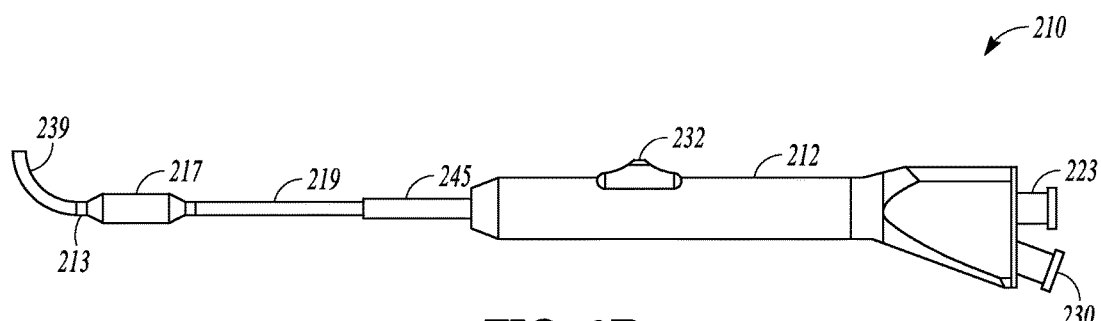
FIG. 2D illustrates a perspective view of a balloon dilation catheter of the invention.
Figure 2E:
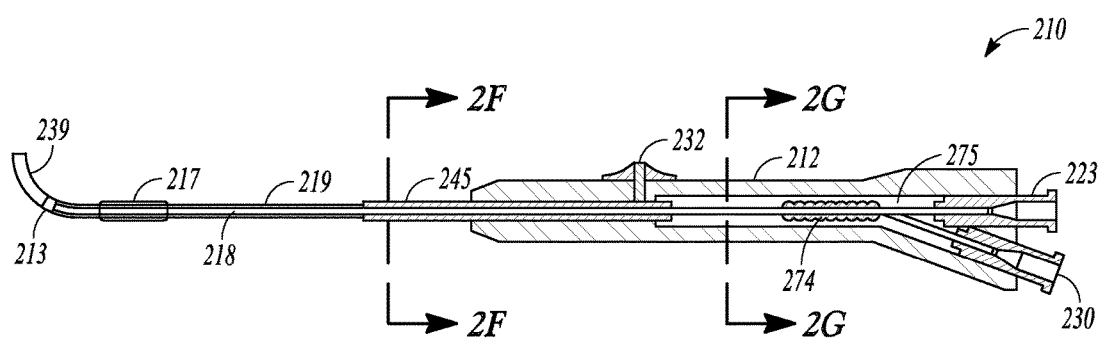
FIG. 2E illustrate a cut-away view of a balloon dilation catheter of the invention.
Figure 2F:
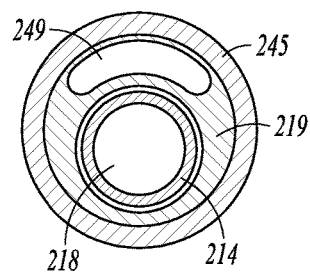
FIGS. 2F and 2G illustrate a cross-sectional profile of two different positions taken along lines 2F-2F and 2G-2G, respectively, of the balloon dilation catheter shown in FIG. 2E.
Figure 2G:
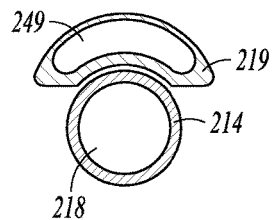

FIGS. 2A-2G illustrate another embodiment of the invention represented as balloon dilation catheter 210. FIGS. 2A-2C shows partial cut-away views of a distal end portion of catheter 210 illustrating a sequential extension and dilation of balloon 217, FIG. 2D illustrates a perspective view of catheter 210, FIG. 2E illustrate a cut-away view of catheter 210, and FIGS. 2F and 2G illustrate a cross-sectional profile of two different positions along the length of catheter 210.

Balloon dilation catheter 210 includes handle 212, tubular guide 214 defining lumen 218 and including distal end 220 and distal tip 221, sleeve member 219, inflation port 230, and suction port 223 and these portions operate and have functions similar to those described in relation to dilation catheter 10. Catheter 210 also includes guidewire 239, which is directed and situated through port 223, along the length of lumen 218, and out distal tip 221 and distal sleeve portion 213.

Figure 8:
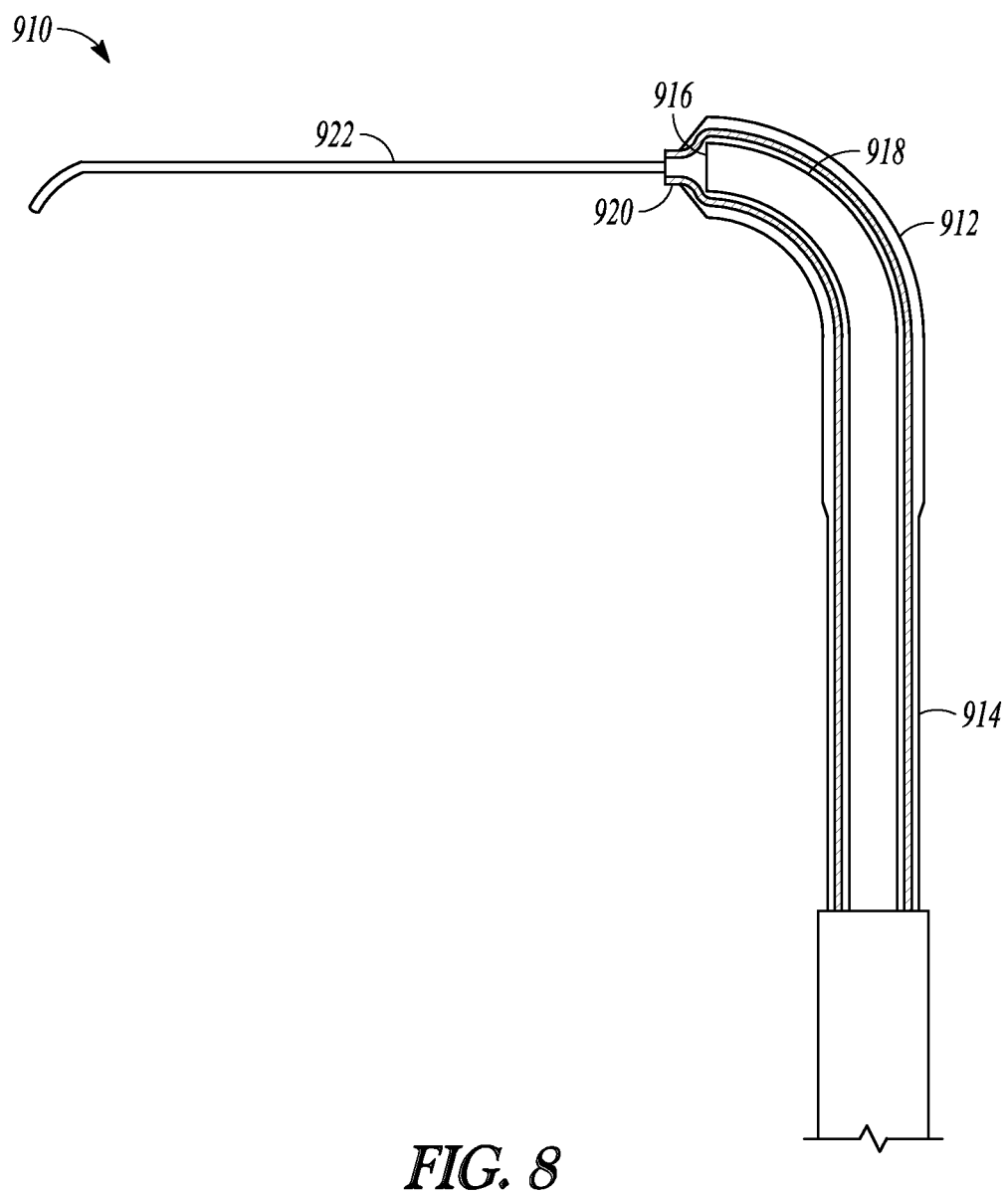
FIG. 8 illustrates a distal end of a balloon dilation catheter of another embodiment.

In some embodiments, a guidewire is not directed through the suction port but instead, an elongate member that is flexible, soft, compliant, deflectable, or malleable is an attached permanent portion of the balloon dilation catheter by, for example, being attached to the sleeve portion (e.g., attached to the distal end of the sleeve portion), secured to the tubular guide, or secured to a lever on the handle which can be advanced in order to advance the guidewire distally relative to the tubular guide or sleeve member. FIG. 8 illustrates a distal portion of balloon dilation catheter 910 which is just one embodiment of a balloon dilation catheter of the invention. Balloon dilation catheter 910 includes balloon 912 situated on the distal end of sleeve member 914 and arranged over distal end 916 of tubular guide 918, similar to the embodiments of the invention illustrated in FIG. 2A. In this embodiment, however, elongate member 922 is attached to distal end 920 of sleeve member 914. When sleeve member 914 is advanced or extended off of distal end 916, elongate member 922 can be used to probe sinus passageways. In some embodiments, the elongate member is pre-shaped or is slightly malleable so that it can hold a shape imparted to it by a user of the catheter. In further embodiments, the elongate member is additionally or alternatively flexible, compliant, soft, and deflectable so that it can be used to gently probe sinus passageways.

Turning back to catheter 210, balloon 217 of catheter 210 is situated closer to the distal end of sleeve member 219 compared to the embodiment illustrated in FIGS. 1A and 1B. Hence, distal sleeve portion 213 is shorter than the distal sleeve portion illustrated in FIGS. 1A and 1B. Distal sleeve portion 213 has a smaller inner diameter than the more proximal portions of sleeve member 219 and only slightly larger than the outer diameter of guidewire 239. Hence, the distal end of sleeve member 219 "necks down" around guidewire 239 so that distal sleeve portion 213 tracks over guidewire 239 when sleeve member 219 is extended from a more retracted position.

Distal end 220 is malleable yet relatively more rigid than distal sleeve portion 213 or guidewire 239. Distal end 220 may be manually formed into a variety of configurations so that tubular guide 214 can be adapted for a given application (e.g., shapes that accommodate a patient's anatomy).

Examples of suitable shapes into which tubular guide 214 can be formed include "U" shapes where distal tip 221 bent back in a retrograde fashion. Such a shape may be useful in accessing hard-to-reach ostia or other structures (e.g., the maxillary ostium or the infundibulum via a transnasal route).

Distal sleeve portion 213 and the inner surface 247 of balloon 217 is made of a material that is more complaint and deflectable than guidewire 239 so that distal sleeve portion 213 and balloon 217 can track over guidewire 239 during extension without pulling on guidewire with an undesirable amount of force that could dislodge guidewire 239 from a desired position. In some embodiments, the distal sleeve portion and inflatable balloon portion is more rigid than the guidewire. In some embodiments, the outer surface of the balloon is made of a material that is less compliant than the inner surface so that the balloon behaves as a non-compliant balloon during inflation.

Sleeve member 213 includes or is attached to proximal sleeve portion 245. Proximal sleeve portion 245 is made of a material more rigid (e.g., stainless steel) than the other portions of sleeve member 213. Proximal sleeve portion 245 reinforces the proximal portions of sleeve member 213 and provides sleeve member 213 with increased column strength.

FIG. 2A illustrates a distal portion of catheter 210 when catheter 210 is in a fully retracted position. In this retracted position, balloon 217 overlies distal end 220 and distal tip 221 of tubular guide 214 and distal sleeve portion 213 abuts distal tip 221.

FIG. 2B illustrates the extension of sleeve member 219 longitudinally along directions 241 and 242. During extension, distal sleeve portion 213 and balloon 217 are advanced off of distal end 220 of tubular guide 214 and track along the exposed distal portions of guidewire 239. Distal sleeve portion 213 and balloon 217 are mechanically linked to pushing member 232 (illustrated in FIG. 2D). Advancing pushing member 232 distally relative to handle 212 causes distal sleeve portion 213 and balloon 217 to advance.

FIG. 2C illustrates catheter 210 in an extended state. Balloon 217 has been inflated such that non-complaint outer surface 248 of balloon 217 has increased in diameter compared to the illustrations of FIGS. 2A and 2B.

FIG. 2E illustrates a cross-section view of catheter 210. Sleeve member 219 is mechanically linked to pushing member 232 in a manner similar to that described in relation to FIGS. 3B and 4 of U.S. Pat. Pub. 2010/0312101 (the entire teachings of which are incorporated herein by reference).

FIG. 2F illustrates a cross-section view of catheter 210 at the point indicated as "2F" in FIG. 2E. Proximal sleeve portion 245 defines a lumen in which resides sleeve member 219. Sleeve member 219, in turn, defines lumen 218, in which resides tubular guide 214, and inflation lumen 249. Inflation lumen 249 is in fluid communication with balloon 217 and inflation port 230. Inflation lumen 249 is placed in fluid communication with inflation port 230 in a manner similar to that illustrated in FIG. 4 of U.S. Pat. Pub. 2010/0312101. Specifically, proximal sleeve portion 245 includes helical portion 274 in recessed region 275 of handle 212. Helical portion 274 facilitates the distal advancement or extension and proximal retraction of sleeve member 219 along tubular guide 214, yet still maintains fluid communication with port 230. Helical portion 274 is in the shape of a helix that wraps around tubular guide 214 and is configured to elongate and contract upon movement of pushing member 232. Helical portion 274 may be formed by "skiving" away a portion of proximal sleeve portion 245.

FIG. 2G illustrates a cross-sectional view of catheter 210 at the point indicated as "2G" in FIG. 2E. For clarity, portions of handle 212 have been omitted from FIG. 2G. In this view, tubular guide 214 defines lumen 218 and is situated next to a portion of sleeve member 219 that defines inflation lumen 249.

FIGS. 2H-2K illustrate various cross-sectional views (sagittal plane) of a frontal sinus of a subject undergoing treatment with balloon dilation catheter 210. While positions for catheter 210 are described herein, it is understood that substantially the same positions are employed for deployment of other catheter embodiments of the invention. The cross-sectional views illustrate a nasal passageway 200, a frontal recess 201, and a frontal sinus cavity 203. While FIGS. 2H-2K illustrate the treatment of a drainage pathway for a frontal sinus cavity, it will be understood that similar methods can be used to treat the drainage pathways of the other sinus cavities (e.g., maxillary and sphenoid sinus cavities).

Figure 2H:
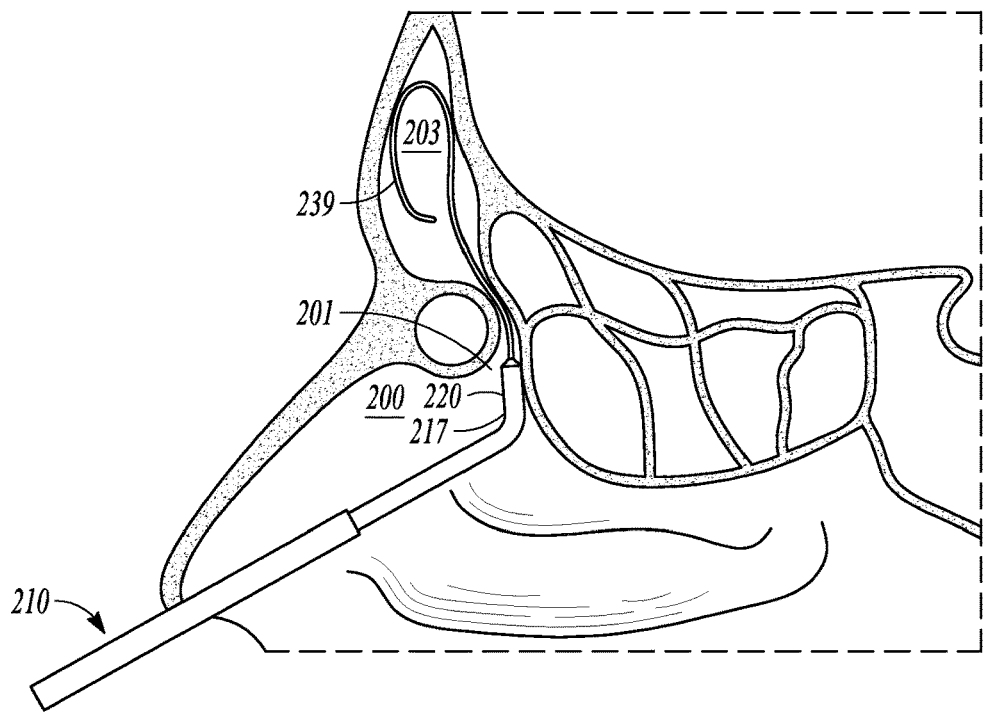
FIGS. 2H-2K illustrate various cross-sectional views of a frontal sinus of a subject undergoing treatment with a balloon dilation catheter of the invention.

As shown in FIG. 2H, balloon dilation catheter 210 is inserted into the nasal passageway 200 while catheter 210 is in a retracted position with balloon 217 in a deflated state. Distal end 220 of tubular guide 214 is then positioned within or near the entrance to frontal recess 201 and a distal end portion of guidewire 239 is directed through catheter 210 and positioned in frontal sinus cavity 203. This positioning of tubular guide distal end 220 and guidewire 239 may be accomplished under endoscopic visualization using a conventional endoscope such as a Hopkins rod-type endoscope that is positioned alongside balloon dilation catheter 210. Alternatively, or in addition, imaging guidance or CT imaging systems may be use to position end 220 or guidewire 239.

Confirmation of accurate positioning of guidewire 239 within frontal sinus cavity 203 can be accomplished by fluoroscopically viewing guidewire 239. If correctly positioned, the distal end portion of guidewire 239 will be seen to loop within the frontal sinus cavity 203. If fluoroscopy does not confirm the correct position, the guidewire 239 is retracted back into catheter 210 (optionally, catheter may also be repositioned) and then passed into another passage suspected of being the entrance to frontal sinus cavity 203 and confirmation is again checked via fluoroscopic images.

As an alternative or supplement to fluoroscopic confirmation, guidewire 239 may be a light-emitting guidewire such as that disclosed in U.S. Pat. Pub. 2007/0249896, which is incorporated by reference herein.

Figure 2I:
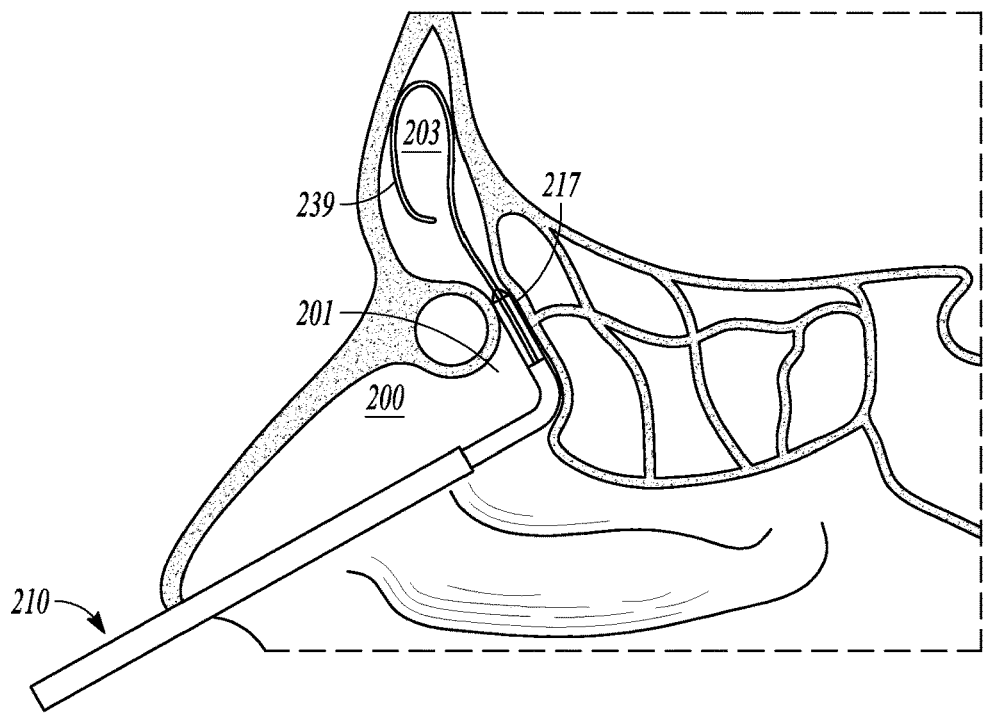
Figure 2J:
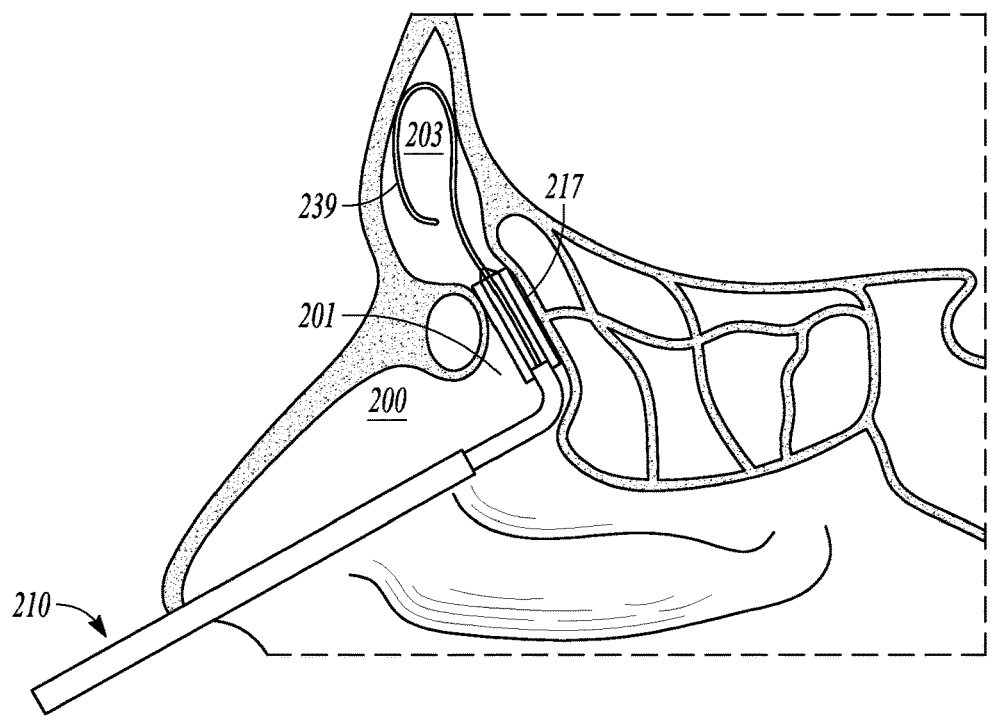

Once guidewire 239 is placed within frontal sinus cavity 203, pushing member 232 is advanced in the distal direction thereby advancing distal sleeve portion 213 along guidewire 239 until balloon 217 is located at the desired dilation site (as shown in FIG. 2I). Because distal sleeve portion 213 has been "necked down" to closely track guidewire 239, distal sleeve portion 213 will be less likely to scrape or otherwise injure sinus tissue as it is advanced along guidewire 239.

After balloon 217 is positioned in the desired location (e.g. in frontal recess 201, as shown in FIG. 2I), balloon 217 is inflated. Inflation is accomplished by coupling an inflation device (not shown) to inflation port 230. The inflation device may include a syringe or the like that is depressed to direct a fluid into inflation lumen 249 and into the interior of balloon 217, thereby causing inflation of balloon 217 to the state illustrated in FIG. 2J and widening or remodeling of the bone and other tissue defining frontal recess 201. Pressures typically used to accomplish widening or remodeling of frontal recess 201 are within the range of about 3 atmospheres to about 18 atmospheres, about 8 to about 14 atmospheres, or about 12 atmospheres. Balloon 217 may be inflated only a single time or, alternatively, may be inflated, deflated, and inflated again a plurality of times in order to achieve the desired degree of widening. Each inflation step may be performed after positioning balloon 217 in a different position within frontal recess 201.

Figure 2K:
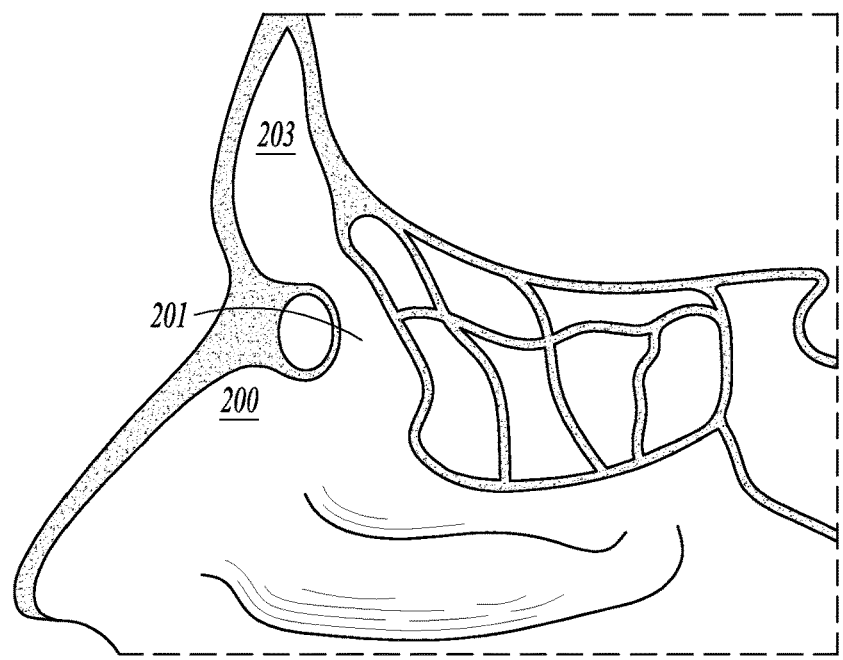

After frontal recess 201 has been widened or otherwise remodeled, balloon 217 is deflated and removed as illustrated in FIG. 2K. The now widened frontal recess 201 illustrated in FIG. 2K is believed to restore the drainage and aeration function and health of frontal sinus cavity 203.

In certain patients, treatment of one or both frontal sinuses 104 as described above may be adequate. In other patients, additional or alternative sinuses may need to be treated, particularly the maxillary and/or anterior ethmoid sinuses by dilation of the maxillary ostium or the ethmoid infundibulum. In such patients, a combination procedure may be well suited. Distal end 220 of tubular guide 214 can be shaped to accommodate treatment of the drainage pathways of those other sinus cavities. Alternatively, or in addition to, the catheters described herein can be used in combination with one of the devices or systems described in U.S. Pat. No. 7,520,876 or U.S. Pat. Pub. 2008/0172033, the entire teachings of which are incorporated herein by reference. Alternatively, or in addition to, the frontal or other sinuses could be treated more conventionally using surgical techniques such as, for instance, functional endoscopic sinus surgery (FESS) or via pharmaceutical substances.

Also, the sphenoid sinus outflow tracts could be dilated with one or more of the catheters described herein. It is also contemplated that the catheters described herein could be used to dilate the maxillary sinus outflow tract via a trans-canine fossa route. Suitable access tools are described in co-pending U.S. patent application Ser. No. 12/038,719, filed on 27 Feb. 2008, published as U.S. Pat. Pub. 2009/0216196, and which is incorporated in its entirety by reference herein.

Another embodiment of the invention is illustrated in FIGS. 6A-6D as balloon dilation catheter 610. As with the previously described embodiments, catheter 610 includes handle 612 on which is mounted sleeve pushing member 632, sleeve member 619 that includes balloon 617 and proximal sleeve portion 645, malleable tubular guide 614, inflation port 630, and sleeve pushing member 632.

Figure 6A:
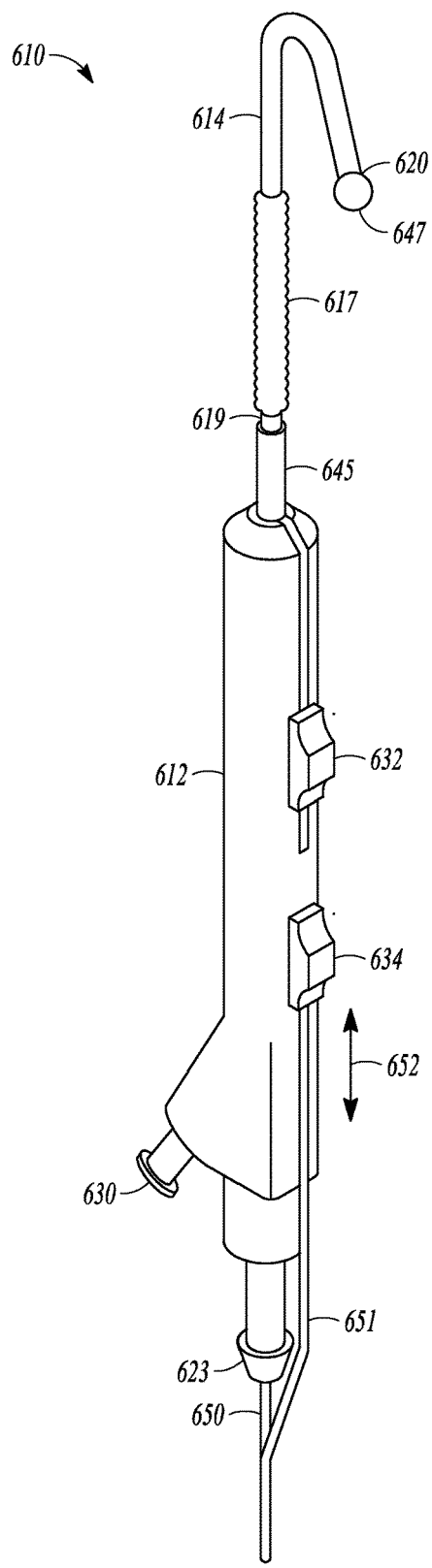
FIGS. 6A-6E illustrate a balloon dilation catheter of another embodiment.
Figure 6B:
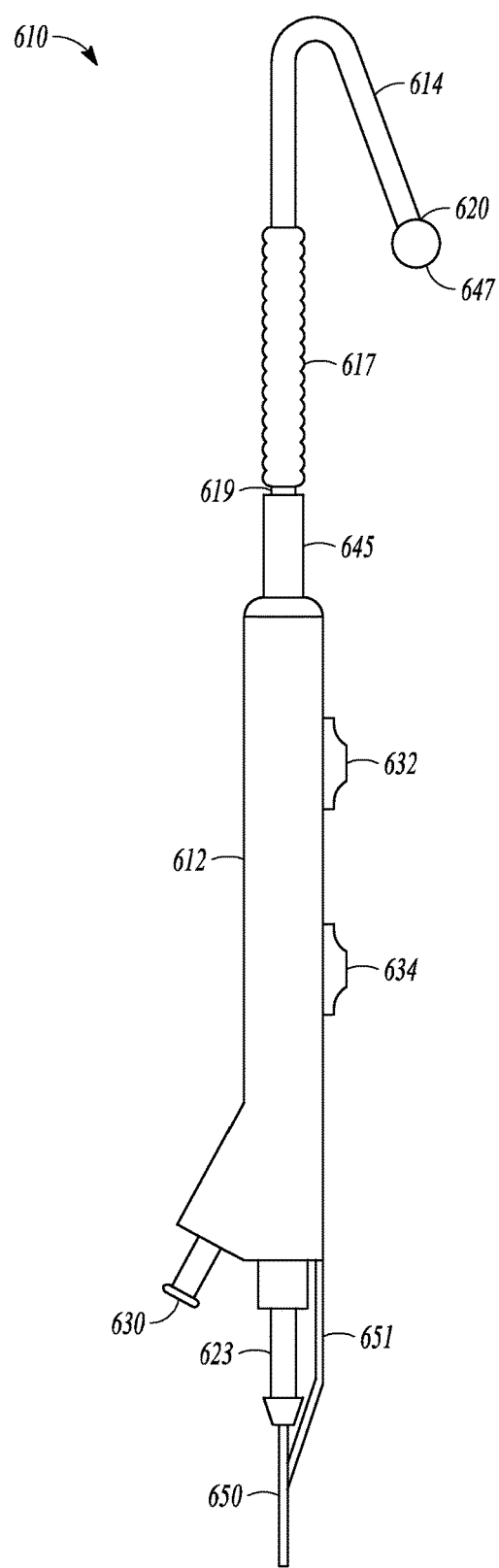
Figure 6C:
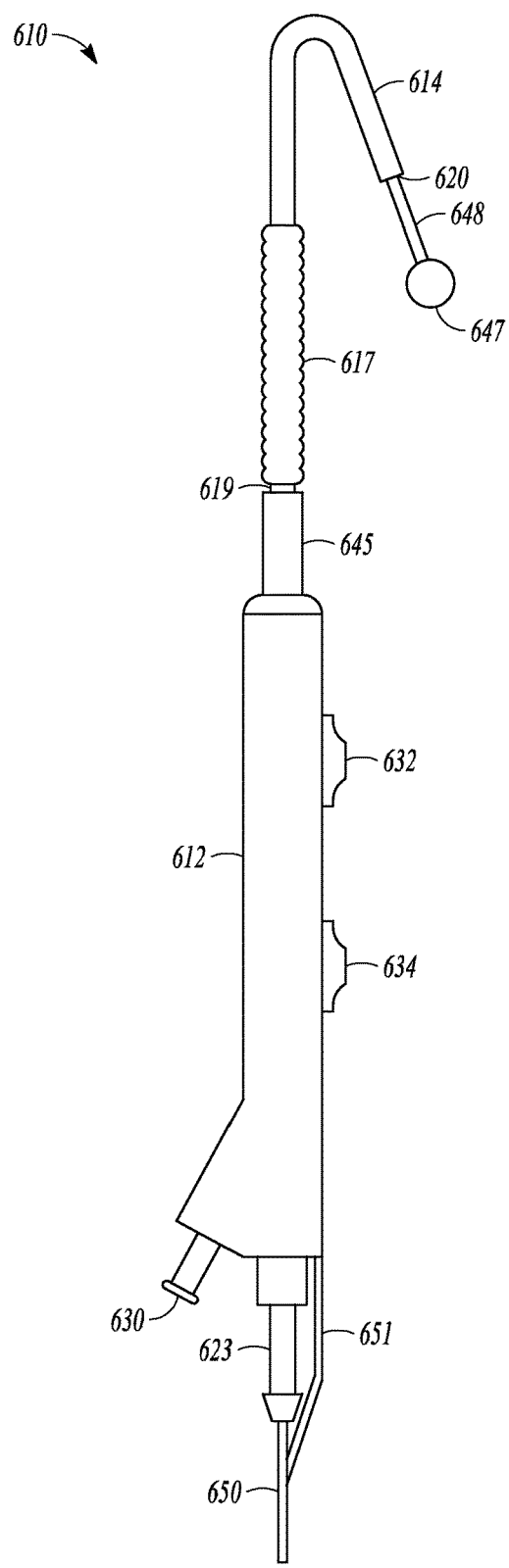

Catheter 610 also includes a tubular guide extension in the form of advanceable ball tip 647 and distal rod 648 (illustrated in FIG. 6C). Advanceable ball tip 647 is positioned at the end of distal rod 648. Distal rod 648 is mechanically linked to proximal rod 650 that extends through port 623. Proximal rod 650 is mechanically linked to pushing rod 651. Pushing rod 651 is mechanically linked to tip-advancement pushing member 634. Distal rod 648 is made of a relatively rigid material (e.g., stainless steel) that provides balloon 617 improved column support when it is tracked off of distal end 620 of tubular guide 614, compared to embodiments of the invention where a balloon is tracked off a tubular guide and onto a relatively flexible member (e.g., a guidewire). In some embodiments the distal rod is made of a rigid, yet malleable material. In some embodiments, rods and other components used to mechanically link the proximal rod to the tip-advancement pushing member are internal to the handle.

Figure 6D:
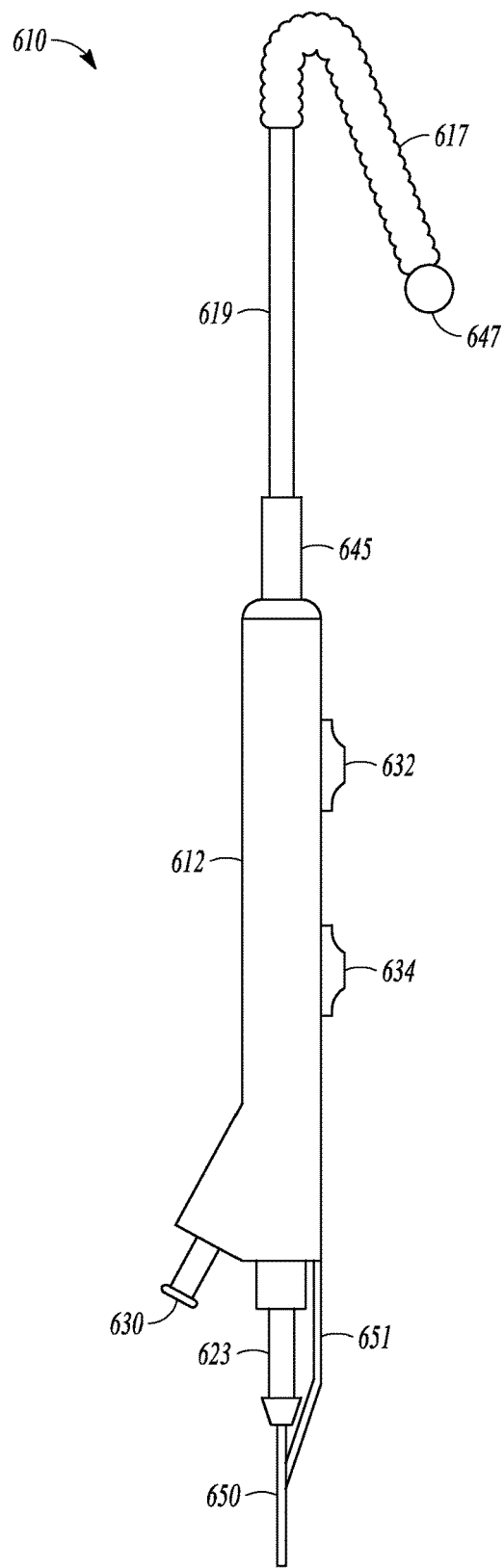

Advanceable ball tip 647 and distal rod 648 can be extended and retracted from tubular guide 614 and balloon 617 and sleeve member 619 can be advanced off of tubular guide 614 and over distal rod 648, as illustrated in FIGS. 6B-6D which show a sequence of three profile views of catheter 610. When tip-advancement pushing member 634 is directed proximally and distally along direction 652 (shown in FIG. 6A), advanceable ball tip 647 and distal rod 648 are directed in and out of distal end 620 of tubular guide 614. FIG. 6B illustrate catheter 610 with the tubular guide extension in a fully retracted position, with distal rod 648 (not shown) fully retracted into tubular guide 614 and ball tip 647 abutting distal end 620 of tubular guide 614. FIG. 6C illustrates catheter 610 with the tubular guide extension in an extended position, with distal rod 648 extended out of tubular guide 614 and ball tip 647 no longer abutting distal end 620. FIG. 6D illustrates catheter 610 with balloon 617 and sleeve 619 in an extended position. Balloon 617 has been advanced over tubular guide 614 (not shown in FIG. 6D), off of its distal end 620, and now abuts ball tip 647.

The tubular guide extension, comprising distal rod 648 and ball tip 647, of catheter 610 enables a user to advance balloon 617 off of tubular guide 614 in order to increase the effective "reach" of catheter 610. Because distal rod 648 is made of a rigid material, even when extended from tubular guide 614 the tubular guide extension can provide improved tactile feedback to a user of catheter 610 in order to assist in probing sinus anatomy. When a desired dilation position is identified, balloon 617 can be tracked to that site by advancement over and off of tubular guide 614 and onto distal rod 648.

Figure 6E:
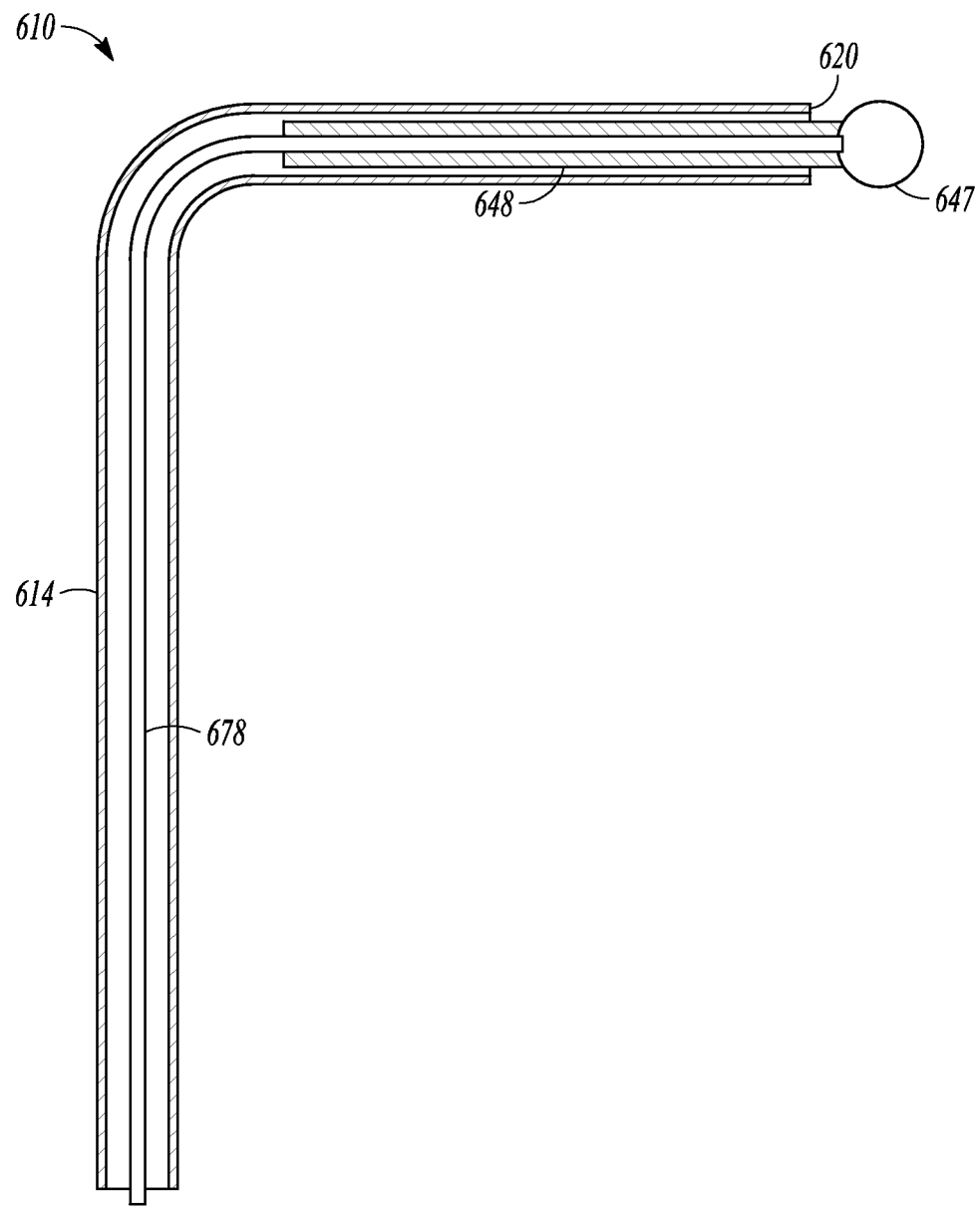

FIG. 6E illustrates a cross-section view of the distal end of catheter 610 in which the distal portion of tubular guide 614 has been positioned in a 90-degree bend relative to the proximal portion of tubular guide 614. Ball tip 647 is attached to distal rod 648. Distal rod 648 is in turn attached to pushing wire 678. Pushing wire 678 lies within the lumen defined by tubular guide 614 and the proximal portion of pushing wire 678 is attached to a distal end of proximal rod 650. Pushing wire 678 is flexible so that it can negotiate bends or other deformation placed in the distal end of tubular guide 614, yet has enough column strength so that it can force distal rod 648 in and out of distal end 620 of tubular guide 614. When pushing member 634 is directed proximally and distally, that motion in turn moves rods 651 and 650 as well as wire 678 and tip 647 since wire 678 is attached to the distal end of rod 650 and tip 647.

While the above embodiments of the invention have been described as balloon dilation catheters having a sleeve member and balloon that are advanced longitudinally along a tubular guide, some embodiments of the present invention include balloon dilation catheters having a sleeve member and balloon that can be advanced both longitudinally and circumferentially about a tubular guide. Some of these circumferentially-positionable catheter embodiments include a handle having a pushing member that can be translated distally and proximally along the longitudinal axis of the handle as well as circumferentially around the longitudinal axis. In this way, a user of a circumferentially-positionable catheter embodiment of the invention can hold the catheter in one hand and use a single digit to both advance the balloon distally off of a tubular guide and then pivot the balloon about the axis of the tubular guide. Such an embodiment is illustrated in FIG. 7.

Figure 7:
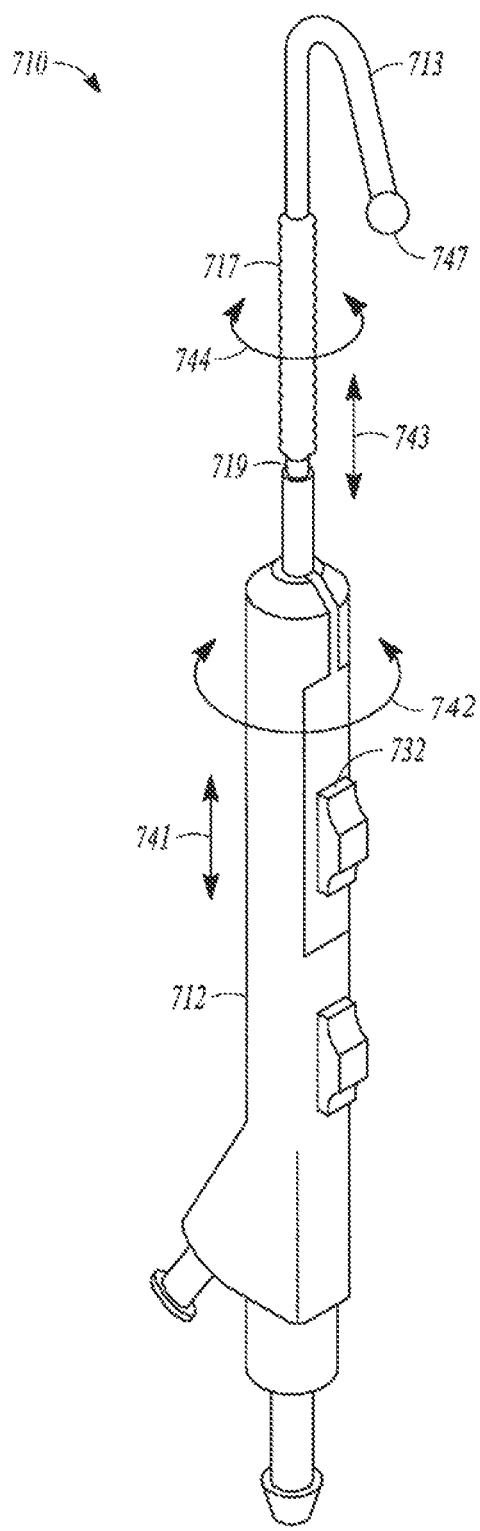
FIG. 7 illustrates a balloon dilation catheter of another embodiment.

FIG. 7 illustrates balloon dilation catheter 710. Balloon dilation catheter 710 is similar to balloon dilation catheter 10 of FIG. 1A in that it includes a sleeve member that, when in a fully retracted position, abuts the distal end of the tubular guide and, in an extended position, the distal sleeve portion and its ball tip 747 translate off of the distal end of the tubular guide.

One difference between balloon dilation catheter 710 and catheter 10 is that catheter 710 includes pushing member 732 which can be translated in at least two different dimensions in order to move sleeve member 719 and its components (e.g., distal sleeve portion 713 and balloon 717) in a similar manner. For example, moving pushing member 732 along longitudinal direction 741 causes portions of sleeve member 719 to move along the longitudinal length of the tubular guide (not illustrated) parallel to direction 743. Similarly, moving pushing member 732 along circumferential direction 742 about handle 712 causes portions of sleeve member 719 to move in circumferential direction 744 about the longitudinal axis of the tubular guide.

This ability to both translate a sleeve member off of a tubular guide and pivot it about the tubular guide can increase a balloon dilation catheter's probing ability, particularly if the sleeve member is attached to a soft, deflectable, or malleable tip portion (e.g., a soft or malleable guidewire). Any of the balloon dilation catheter embodiments described herein can include a sleeve member which can move both longitudinally along and circumferentially about a tubular member.

Figure 3A:
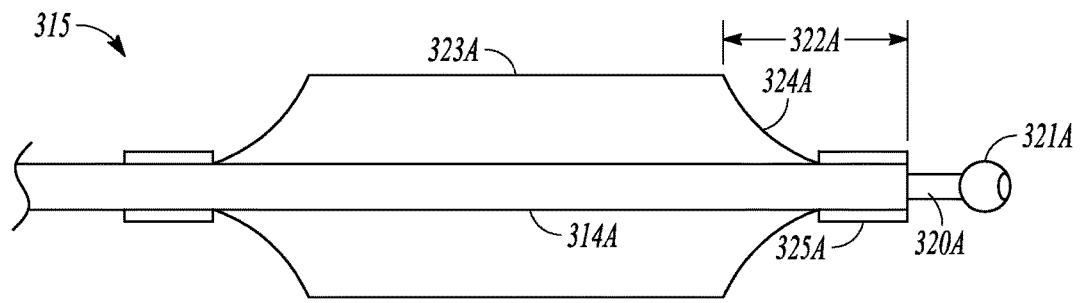
FIG. 3A illustrates a prior art balloon.
Figure 3B:
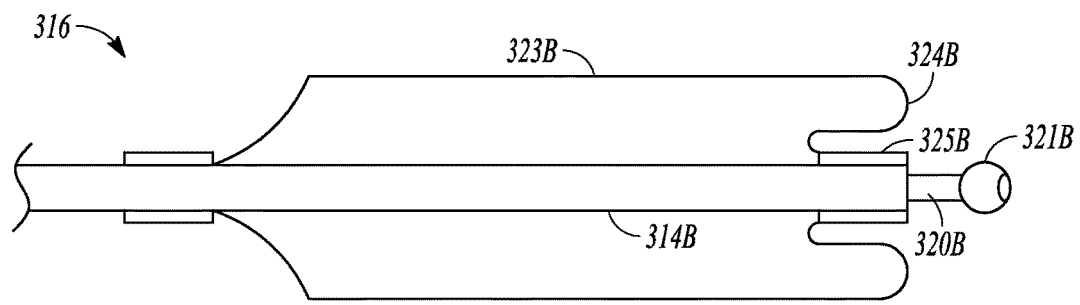
FIGS. 3B and 3C illustrates two different balloons embodiments.
Figure 3C:
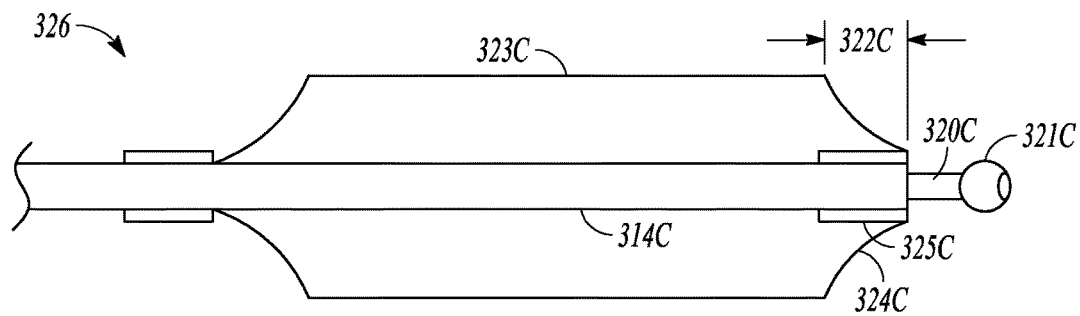

Inventive balloon embodiments disclosed herein include balloon embodiments 316 and 326 shown in FIGS. 3B and 3C, respectively.

One prior art balloon is shown at 315 in FIG. 3A. Prior art balloon 315 has a distal waist 325A that is bonded to sleeve member 314A. As sleeve member 319A is advanced over tubular guide 320A, distal waist 325A abuts ball tip 321A of tubular guide 320. When abutting ball tip 321A, waist 325A causes a set-back in balloon body 323A of about distance 322A. Distance 322A is equal to the length of waist 325A and the length of shoulder 324A.

It has been recognized that, for some purposes, having the full-dilation diameter of a balloon as close to the distal end of a tubular guide would be beneficial. In other words, it would be useful to keep distance 322A as small as possible.

FIG. 3B illustrates one embodiment of the invention that includes balloon 316. Balloon 316 includes distal waist 325B which is bonded to sleeve member 314B. Balloon 316 is shaped such that, when inflated, balloon 316 has wings 324B that roll forward and over waist 325B. Wings 324B have an outer diameter that is approximately equal to that of balloon body 323B. In this manner, when inflated, the effective inflation diameter of balloon 316 can be brought as close to ball tip 321B when sleeve member 314B is translated distally along tubular guide 320B.

FIG. 3C illustrates another embodiment of the invention that includes balloon 326. Balloon 326 includes distal waist 325C which is bonded to sleeve member 314C. Distal waist 325C is invaginated or folded under shoulder 324C. Invaginating distal waist 325C reduces distance 322C between the balloon body 323C and ball tip 321C, relative to a similar balloon that does not include an invaginated distal waist (e.g., the embodiment illustrated in FIG. 3A).

Hence, some embodiments of the present invention include the balloon catheters described herein having a balloon bonded to a sleeve member as illustrated in FIG. 3A. Alternatively, other embodiments of the present invention include the balloon catheters described herein having a balloon bonded to a sleeve member as illustrated in either of FIG. 3B or 3C. Furthermore, other embodiments of the present invention include balloon dilation catheters substantially as described in U.S. Pat. Pub. 2010/0312101, which was filed by John Drontle and Anthony Hanson on 5 Jun. 2009, assigned U.S. application Ser. No. 12/479,521, and is incorporated in its entirely herein by reference, but having a balloon portion attached to a sleeve member (or the "inner shaft" of the embodiments described by Drontle, et al. in US2010/0312101") in the manner described with respect to FIG. 3B or 3C.

Figure 4:
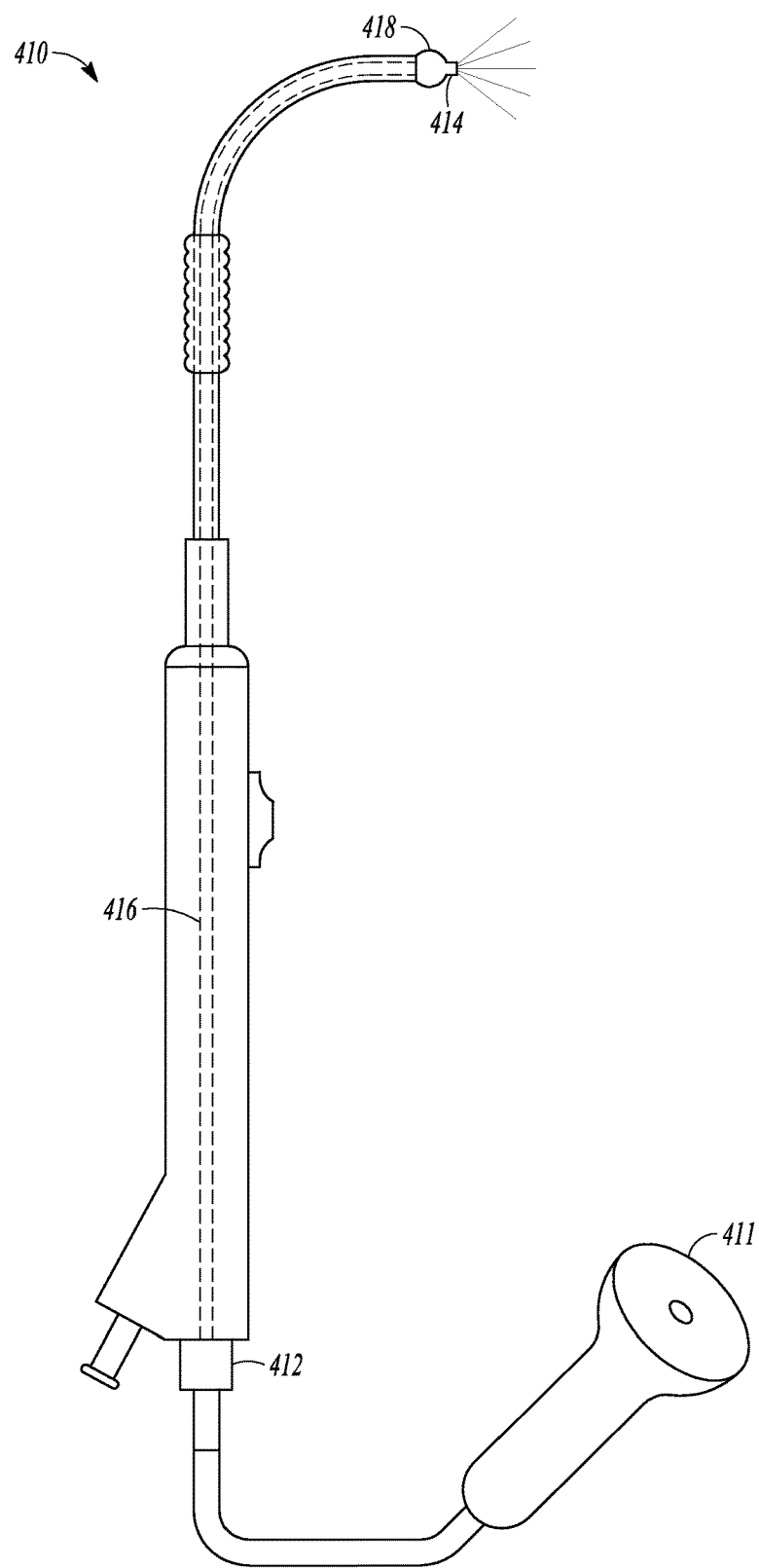
FIG. 4 illustrates a balloon dilation catheter according to one embodiment.

Another embodiment of the invention is illustrated in FIG. 4 which illustrates balloon dilation catheter 410 which is a balloon dilation catheter taught in US2010/0312101. Catheter 410 includes fiber-optic endoscope 411. Distal end 414 of endoscope 411 has been inserted through suction port 412, along the inner lumen 416, and to the distal end 418 of endoscope 410. Combining endoscope 411 with catheter 410 in this way enables a user of catheter 410 to view anatomy in front of endoscope 411. In some embodiments of the invention, a Tuohy-Borst adaptor is mounted to port 412 which allows a user to lock the position of distal end 414 of endoscope relative to endoscope 411. In further embodiments, a Y-adaptor is mounted to port 412 so that endoscope 411 can be directed through one arm of the adaptor and a cleaning fluid (e.g., saline or water) can be directed through the other arm to clean distal end 414 of endoscope 411 during use.

Figure 5:
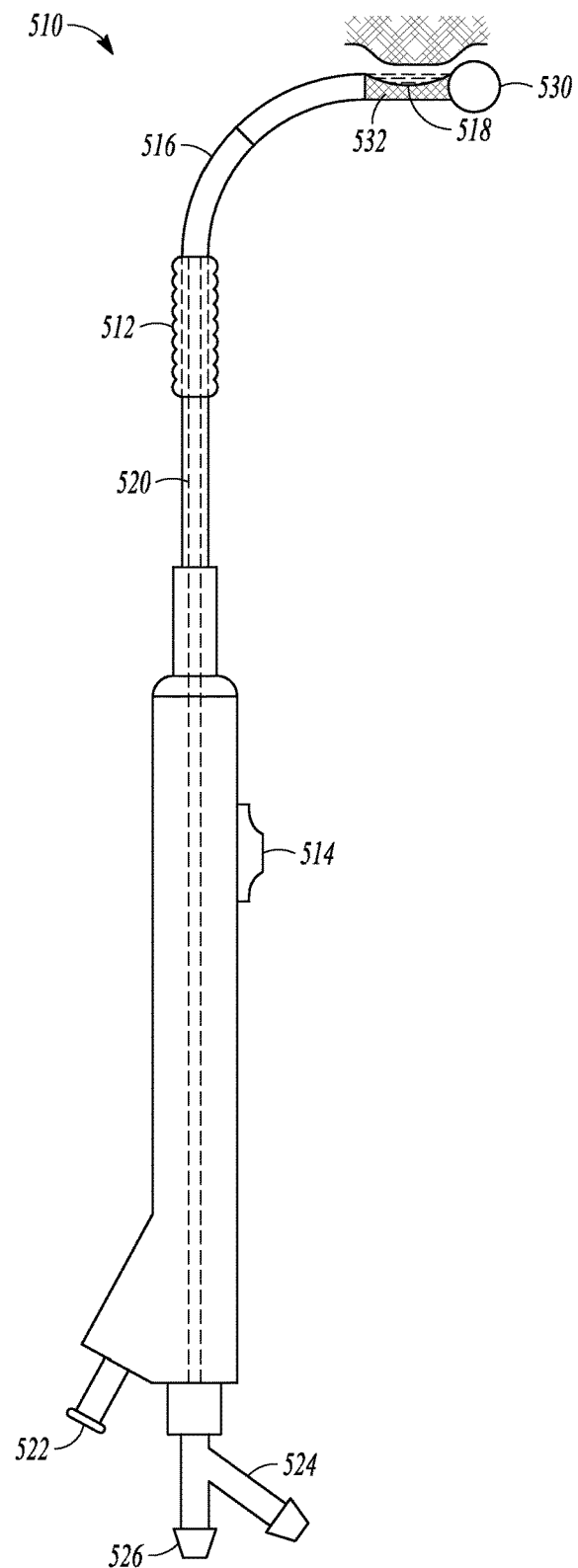
FIG. 5 illustrates a balloon dilation catheter according to another embodiment.

Another embodiment of the invention is illustrated in FIG. 5 as balloon dilation catheter 510. Catheter 510 includes balloon 512 which can be advanced over tubular guide 516 using pusher member 514 in order to dilate tissue in much the same was as is described in the embodiments mentioned previously or as described in US2010/0312101. In addition, catheter 510 includes a debrider function that can macerate tissue and bone and carry the resulting debris out of the surgical field. This is accomplished at notch 518 which provides a passageway between the exterior surface of tubular guide 516 and inner lumen 520 defined by tubular guide 516. As illustrated in FIG. 5, catheter 510 includes ball tip 530 on its distal end. In some embodiments, the catheter includes a pointed tip that is useful for penetrating tissue or bone.

Water or saline is directed through fluid supply port 524, travels up a water supply lumen defined in tubular guide 516, and sprays out from the distal side of notch 518. The distal end of the water supply lumen is pointed back towards the proximal side of notch 518 (i.e., in a retrograde fashion) so that the resulting water jets 532 from the distal side of notch 518 to the proximal side of notch 518. Proximal side of notch 518 is in fluid communication with suction lumen 520 defined by tubular guide 516 and with suction port 526. An inflation device may be connected to inflation port 522.

During use, a practitioner of this embodiment of the invention attaches a water supply line to port 524 and a suction source to port 526. Water travels up the water supply line and is directed backwards so that it travels from the distal to the proximal sides of notch 532. At the proximal side, the attached suction source draws the water back down lumen 520 and out port 526. The water is directed with such force that any tissue or bone that enters notch 518 is cut and macerated by the water. The pressure of the water jets in notch 518, combined with the suction forces at the distal end of lumen 520, result in a water vortex forming in notch 518 which can produce a suction force near notch 518 and assist in drawing loose tissue and bone pieces into the cutting streams of water so that the tissue can be macerated and carried away from the surgical site. The flow rates of the water supplied to notch 518 and the suction force applied to notch 518 are matched so that water and macerated tissues are carried away and do not accumulate in notch 518.

In this manner, catheter 510 provides both a tissue removal function similar to micro debriders commonly used in ENT procedures as well as a balloon-dilation function.

While embodiments of the present invention have been shown and described, various modifications may be made without departing from the scope of the present invention. Relative sizes and dimensions shown in the various figures can be altered in order to suite a specific application. For example, the invention includes balloon dilation catheters that are similar to catheter 610 shown in FIG. 6D but have a balloon that is shorter such that it can be extended completely past the bend in the malleable distal end of the tubular guide. The invention, therefore, should not be limited, except to the following claims, and their equivalents.

What is claimed is:

1. A device for dilating a sinus cavity lumen, comprising:
   a handle having a proximal end and a distal end;
   a guide tube, having a proximal end and a distal end, and extending longitudinally from the distal end of the handle in a distal direction, the distal end terminating in a distal tip, a distal portion of the guide tube being malleable;
   a sleeve member annularly positioned over the guide tube, wherein the sleeve member is movable relative to the guide tube between a retracted position and an extended position and is capable of being advanced over the guide tube and past the distal tip in the extended position, the sleeve member comprising a distal end portion having a diameter smaller than a proximal sleeve portion, and wherein the guide tube is contained inside sleeve member in the retracted and extended positions;
   a balloon secured to the sleeve member, wherein the balloon is moveable relative to the guide tube and extendable and inflatable beyond the distal tip of the guide tube; and
   an elongate member extending from a distal end of the sleeve member.

2. The device of claim 1, wherein the elongate member is malleable.

3. The device of claim 1, wherein the elongate member is flexible or compliant.

4. The device of claim 1, wherein the elongate member is pre-shaped.

5. The device of claim 1, wherein the elongate member is attached to the distal end portion.

6. The device of claim 1, wherein the proximal end of the guide tube is rigid.

7. The device of claim 1, wherein the balloon is positioned at the distal tip in the fully retracted state.

* * * * *